(12) United States Patent
Chin et al.

(10) Patent No.: US 11,712,253 B2
(45) Date of Patent: Aug. 1, 2023

(54) DEVICES AND METHODS FOR SPINAL DECOMPRESSION SURGERY

(71) Applicant: KIC VENTURES, LLC, Malden, MA (US)

(72) Inventors: Kingsley R. Chin, Malden, MA (US); Joshua Finkel-Lopez, Malden, MA (US); Oscar Herrera, Malden, MA (US); Darryl Cambell-Spaulding, Malden, MA (US); Rahul Gawande, Malden, MA (US); Vito Lore, Malden, MA (US)

(73) Assignee: KIC VENTURES, LLC, Malden, MA (US)

( * ) Notice: Subject to any disclaimer, the term of this patent is extended or adjusted under 35 U.S.C. 154(b) by 0 days.

(21) Appl. No.: 17/530,214

(22) Filed: Nov. 18, 2021

(65) Prior Publication Data
US 2022/0160375 A1    May 26, 2022

Related U.S. Application Data

(60) Provisional application No. 63/116,730, filed on Nov. 20, 2020.

(51) Int. Cl.
*A61B 17/16* (2006.01)
*A61F 2/44* (2006.01)

(52) U.S. Cl.
CPC ...... *A61B 17/1671* (2013.01); *A61B 17/1628* (2013.01); *A61B 17/1631* (2013.01); *A61F 2/4405* (2013.01)

(58) Field of Classification Search
CPC .......................... A61F 2/4405; A61B 17/1671
See application file for complete search history.

(56) References Cited

U.S. PATENT DOCUMENTS

| | | | | |
|---|---|---|---|---|
| 3,737,948 A | * | 6/1973 | Van Mil | A22C 21/0023 452/168 |
| 2003/0040746 A1 | * | 2/2003 | Mitchell | A61B 17/7067 606/279 |

(Continued)

OTHER PUBLICATIONS

Definition of "vertebra." Retrieved from the Interneton Feb. 2, 2023: <https://www.merriam-webster.com/dictionary/vertebra>. (Year: 2023).*

*Primary Examiner* — Christian A Sevilla
(74) *Attorney, Agent, or Firm* — AKC Patents, LLC; Aliki K. Collins

(57) ABSTRACT

A method for inserting an interspinous spinal implant into an opened gap between first and second spinous processes of adjacent superior and inferior vertebras, respectively includes the following. First forming an opened gap between a first spinous processes of a superior vertebra and a second spinous processes of an adjacent inferior vertebra by first inserting a decompression knife into diseased areas of the adjacent superior and inferior vertebras, then cutting fascia tissue, then separating soft tissue from bone by rocking the decompression knife back and forth, and then inserting a broach cutter into the diseased areas of the adjacent superior and inferior vertebras and cutting interspinous ligament between the adjacent superior and inferior vertebras. Next, determining and selecting an appropriate sized and shaped interspinous spinal implant for the opened gap by inserting a sizing tool into the opened gap, and sizing the opened gap with the sizing tool. Next, inserting the selected interspinous spinal implant into the opened gap with an insertion tool, and then compressing first and second elongated components of the interspinous spinal implant onto first and second opposite sides of the first and second spinous processes with a compressor tool, respectively. Finally, locking the interspinous spinal implant onto the first and second spinous (Continued)

processes of the adjacent superior and inferior vertebras with a locking driver.

20 Claims, 26 Drawing Sheets

(56) References Cited

U.S. PATENT DOCUMENTS

| | | | | |
|---|---|---|---|---|
| 2005/0113842 A1* | 5/2005 | Bertagnoli | ............ | A61B 17/025 606/90 |
| 2005/0216019 A1* | 9/2005 | Eckman | ......... | A61B 17/320016 606/79 |
| 2006/0276816 A1* | 12/2006 | Eckman | ......... | A61B 17/320708 606/160 |
| 2006/0293662 A1* | 12/2006 | Boyer | ................ | A61B 17/1671 606/249 |
| 2007/0016210 A1* | 1/2007 | Boehm | .............. | A61B 17/1606 606/79 |
| 2008/0228225 A1* | 9/2008 | Trautwein | .......... | A61B 17/1671 606/301 |

* cited by examiner

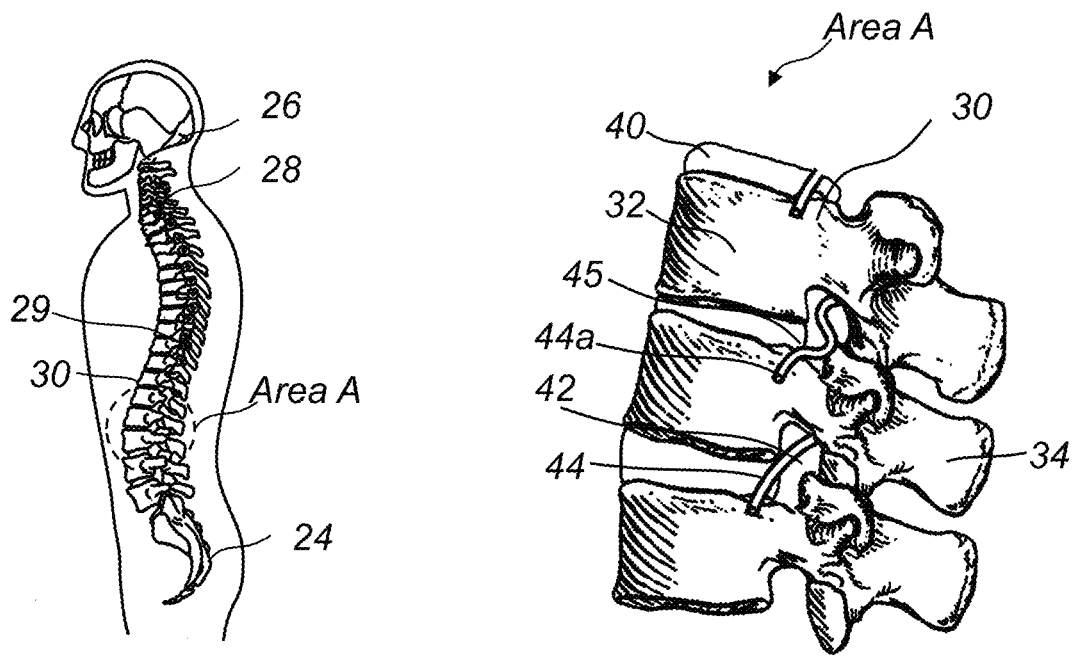
FIG. 1A
FIG. 1B
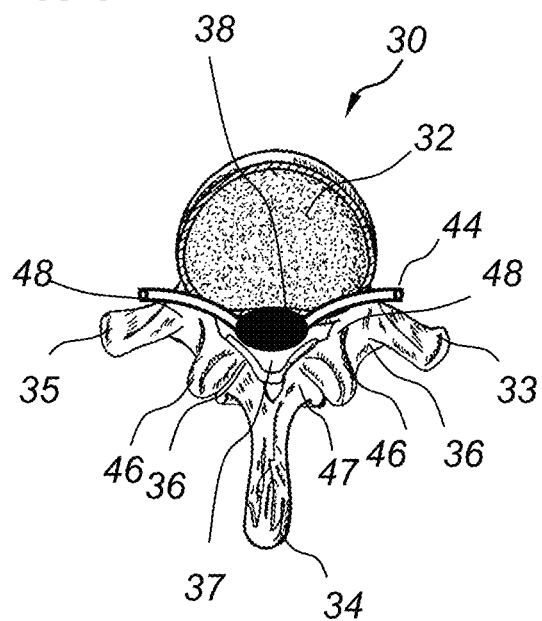
FIG. 1C

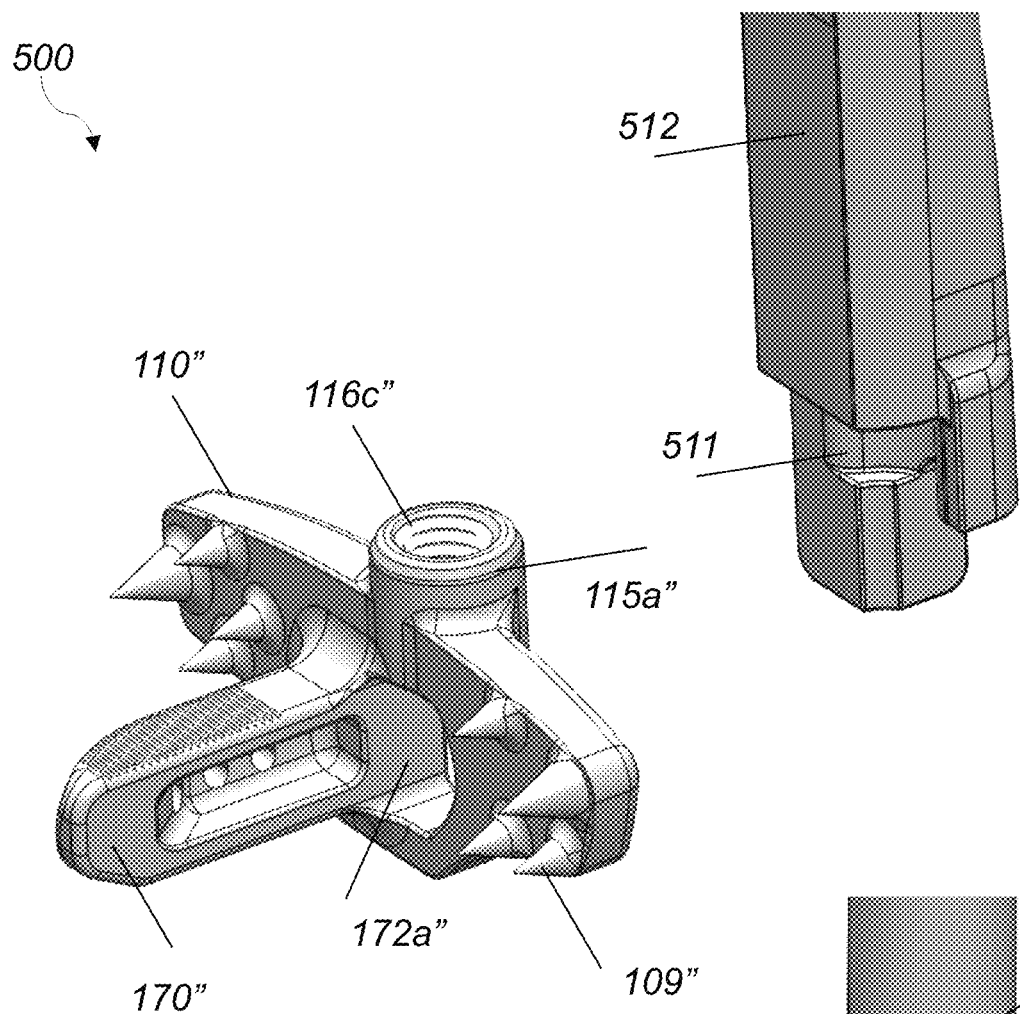
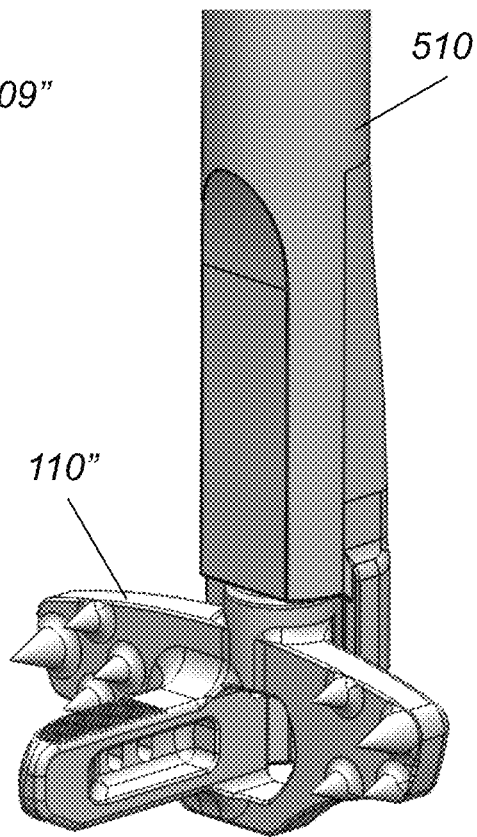
FIG. 15B
FIG. 15C

DEVICES AND METHODS FOR SPINAL DECOMPRESSION SURGERY

CROSS REFERENCE TO RELATED APPLICATIONS

This application claims the benefit of U.S. provisional application Ser. No. 63/116,730 filed Nov. 20, 2020 and entitled "DEVICES AND METHODS FOR SPINAL DECOMPRESSION SURGERY", the contents of which are expressly incorporated herein by reference.

FIELD OF THE INVENTION

The present invention relates to devices and methods for spinal decompression surgery and in particular to devices and methods for spinal decompression, implant insertion, and spinous process stabilization.

BACKGROUND OF THE INVENTION

The human spine is comprised of individual vertebrae 30 that are connected to each other to form a spinal column 29, shown in FIG. 1A. Referring to FIGS. 1B and 1C, each vertebra 30 has a cylindrical bony body (vertebral body) 32, three winglike projections (two transverse processes 33, 35 and one spinous process 34), left and right facet joints 46, lamina 47, left and right pedicles 48 and a bony arch (neural arch) 36. The bodies of the vertebrae 32 are stacked one on top of the other and form the strong but flexible spinal column 29. The neural arches 36 are positioned so that the space they enclose forms a tube, i.e., the spinal canal 37. The spinal canal 37 houses and protects the spinal cord and other neural elements. A fluid-filled protective membrane, the dura 38, covers the contents of the spinal canal. The spinal column is flexible enough to allow the body to twist and bend, but sturdy enough to support and protect the spinal cord and the other neural elements. The vertebrae 30 are separated and cushioned by thin pads of tough, resilient fiber known as inter-vertebral discs 40. Disorders of the spine occur when one or more of the individual vertebrae 30 and/or the inter-vertebral discs 40 become abnormal either as a result of disease or injury. In these pathologic circumstances, spinal decompression surgery, laminectomy, disc resection, disc replacement, and/or fusion of adjacent vertebral segments may be tried to restore the function of the spine to normal, achieve stability, protect the neural structures, or to relieve the patient of discomfort.

The common approach to spinal decompression surgery, laminectomy and/or the removal of a diseased intervertebral disc and replacement with an intervertebral implant is usually via a posterior or an anterior approach. Spinal decompression surgery involves adding space between the vertebrae or removing impinging anatomy (bone or tissue). Laminectomy involves removal of the back portion of the vertebra, i.e., lamina, in order to decompress the posterior neural elements and to enlarge the spinal canal. Disc replacement surgery usually includes laminectomy to first decompress the posterior neural elements and to gain access. After exposure, the intervertebral disc is removed and replaced with an implant device. After spinal decompression surgery, laminectomy and/or disc resection and replacement, vertebral stabilization is usually performed by inserting and attaching spinal stabilization components to the adjacent vertebras. An example of a spinal stabilization device is described in the commonly owned U.S. Pat. No. 9,498,560, issued Nov. 22, 2016 and entitled "Interspinous Spacer Implant" the contents of which are incorporated herein by reference.

There is increasing consensus among surgeons that there is a need to develop devices, instruments, and methods to limit the size of the incision, extensive muscle stripping, prolonged retraction of muscles for visualization, avoidance of neural tissue retraction and injury, and denervation and devascularization that are known to contribute to poorer patient outcome after traditional open surgeries to treat pathologies deep within the body. In many cases these complications lead to permanent scarring and pain that can be more severe than the pain from the initial ailment. Limiting these complications in addition to the operative, general anesthesia, and recovery times are among the goals of this invention and that of percutaneous or minimally invasive surgeries.

Accordingly, there is a need for devices, instruments, and methods that limit the size of the incision, extensive muscle stripping, and prolonged retraction of muscles for visualization, and further provide avoidance of neural tissue retraction and injury, and denervation and devascularization.

SUMMARY OF THE INVENTION

The present invention relates to devices and methods for spinal decompression surgery and in particular to devices and methods for spinal decompression, implant insertion, and spinous process stabilization.

In general, in one aspect, the invention features a method for inserting an interspinous spinal implant into an opened gap between first and second spinous processes of adjacent superior and inferior vertebras, respectively. The method includes the following. First forming an opened gap between a first spinous processes of a superior vertebra and a second spinous processes of an adjacent inferior vertebra by first inserting a decompression knife into diseased areas of the adjacent superior and inferior vertebras, then cutting fascia tissue, then separating soft tissue from bone by rocking the decompression knife back and forth, and then inserting a broach cutter into the diseased areas of the adjacent superior and inferior vertebras and cutting interspinous ligament between the adjacent superior and inferior vertebras. Next, determining and selecting an appropriate sized and shaped interspinous spinal implant for the opened gap by inserting a sizing tool into the opened gap, and sizing the opened gap with the sizing tool. Next, inserting the selected interspinous spinal implant into the opened gap with an insertion tool. The interspinous spinal implant comprises a first elongated component, a second elongated component arranged parallel and opposite the first elongated component. Next, compressing the first and second elongated components of the interspinous spinal implant onto first and second opposite sides of the first and second spinous processes with a compressor tool, respectively. Finally, locking the interspinous spinal implant onto the first and second spinous processes of the adjacent superior and inferior vertebras with a locking driver.

Implementations of this aspect of the invention may include one or more of the following features. Each of the first and second elongated components comprises an elongated body extending along a first direction and an integral post extending from the elongated body perpendicular to the first direction. Each elongated body comprises an opening extending perpendicular to the first direction and the opening is shaped and sized to receive the integral post of the opposite elongated component. Each elongated body comprises a cylindrical projection having an opening configured to receive a set screw and the set screw is configured to secure the position of the integral post of the first elongated component onto the integral post of the second elongated component. The integral post comprises an essentially hollow semi-cylindrical structure. The interspinous spinal implant further comprises top and bottom pins used to secure the first and second elongated components onto the first and second spinous processes, respectively. The decompression knife comprises an elongated shaft having an elongated spade at a distal end and a handle at a proximal end and the elongated spade comprises a concave inner surface, a convex outer surface, and a cutting edge terminating to a sharp point. The elongated spade comprises an electrically insulating material and the cutting edge comprises an electrically conducting material. The cutting edge is connected to a power source and is used to cauterize tissue while cutting. The broach cutter comprises an elongated shaft having a cutting blade at a distal end and a handle at a proximal end. The cutting blade comprises a hollow parallelepiped having a sharp cutting leading edge, a superior surface with a plurality of cutting edges and an inferior surface with a plurality of cutting edges. The insertion tool comprises first and second elongated inserter components and each elongated inserter component comprises an elongated outer tubular component and a stylet configured to slide within the outer tubular component. The outer tubular component comprises a cutout at a distal end shaped and sized to laterally engage a cylindrical projection of the first or second elongated components. The stylet comprises a stylet elongated shaft and a spring surrounding the stylet elongated shaft. A distal end of the stylet elongated shaft has a cross-sectional geometry matching the geometry of a top opening in a set screw of the interspinous spinal implant. The stylet is configured to lock the first or second elongated components onto the distal end of the tubular component, by pressing down and rotating the stylet elongated shaft. The compressor tool comprises first and second components and a jaw component and the first and second components are linked together via a multiaxially rotatable pivot link. The distal end of the second component comprises a screw that attaches to the jaw component. The jaw component comprises a fixed jaw and a movable jaw and the movable jaw is configured to slidably move within the fixed jaw via rotational motion of the second component. The fixed jaw and the movable jaw are configured to engage and compress together the first and second elongated inserter components, respectively.

In general, in another aspect, the invention features a system for inserting an interspinous spinal implant into an opened gap between first and second spinous processes of adjacent superior and inferior vertebras, respectively. The system includes a decompression knife, a broach cutter, an interspinous spinal implant, a sizing tool, an insertion tool, a compressor tool and a locking driver. The decompression knife is used for forming an opened gap between a first spinous processes of a superior vertebra and a second spinous processes of an adjacent inferior vertebra by first inserting the decompression knife into diseased areas of the adjacent superior and inferior vertebras, then cutting fascia tissue, and then separating soft tissue from bone by rocking the decompression knife back and forth. The broach cutter is used for cutting interspinous ligament between the adjacent superior and inferior vertebras. The appropriate sized and shaped interspinous spinal implant is configured to be inserted into the opened gap. The interspinous spinal implant comprises a first elongated component, a second elongated component arranged parallel and opposite the first elongated component. The sizing tool is used for determining and selecting the appropriate sized and shaped interspinous spinal implant for the opened gap. The insertion tool is used for inserting the selected interspinous spinal implant into the opened gap. The compressor tool is used for compressing the first and second elongated components of the interspinous spinal implant onto first and second opposite sides of the first and second spinous processes respectively. The locking driver is used for locking the interspinous spinal implant onto the first and second spinous processes of the adjacent superior and inferior vertebras.

The details of one or more embodiments of the invention are set forth in the accompanying drawings and description below. Other features, objects, and advantages of the invention will be apparent from the following description of the preferred embodiments, the drawings, and the claims.

BRIEF DESCRIPTION OF THE DRAWINGS

Referring to the figures, wherein like numerals represent like parts throughout the several views:

FIG. 1A is a side view of the human spinal column;

FIG. 1B is an enlarged view of area A of FIG. 1A;

FIG. 1C is an axial cross-sectional view of a lumbar vertebra;

FIG. 15B and FIG. 15C depict the approaching and engagement of the inserter component of FIG. 15A with one of the implant components of FIG. 3A, respectively;

DETAILED DESCRIPTION OF THE INVENTION

The present invention relates to devices and methods for spinal decompression, implant insertion, and spinous process stabilization.

Figure 2A:
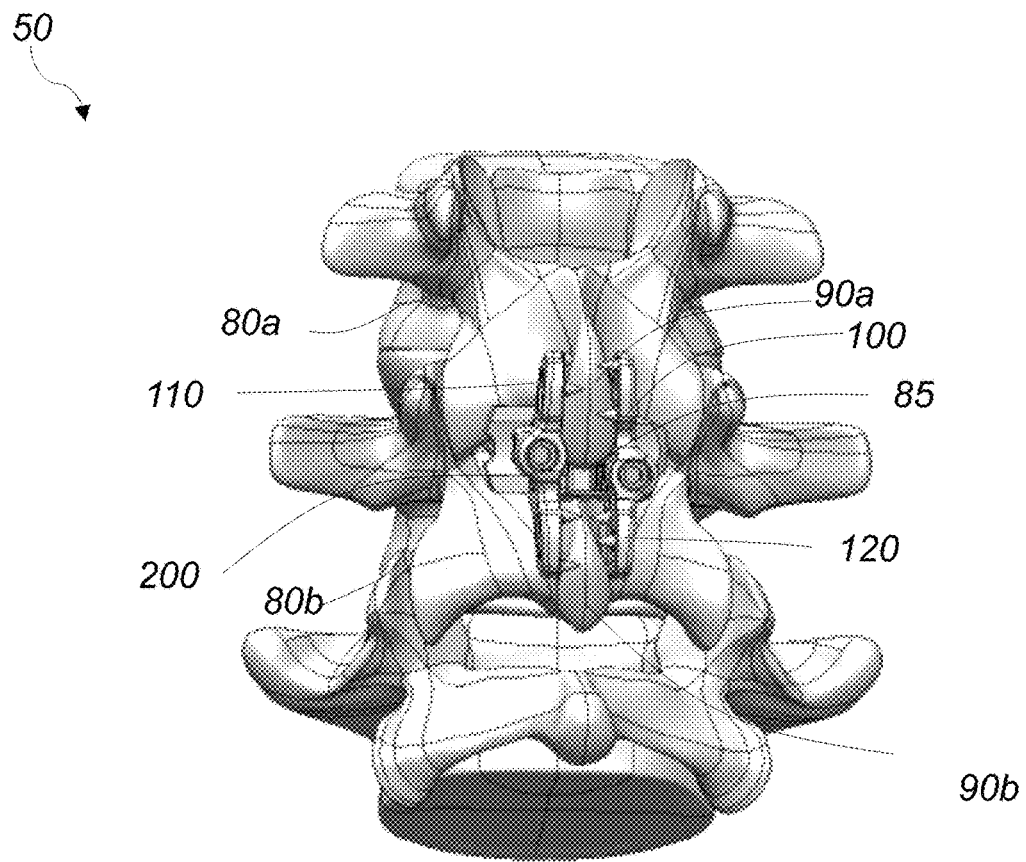
FIG. 2A is a perspective view of an interspinous fixation implant assembly, used to secure two adjacent vertebrae.
Figure 2B:
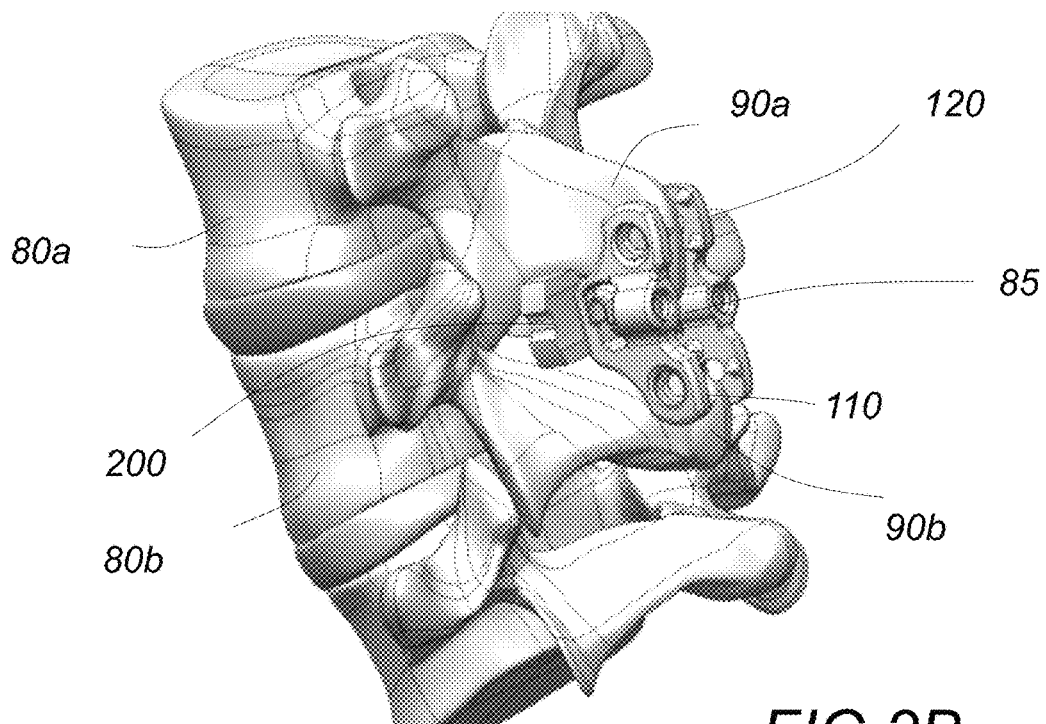
FIG. 2B is perspective side view of the interspinous fixation implant assembly of FIG. 2A.
Figure 3A:
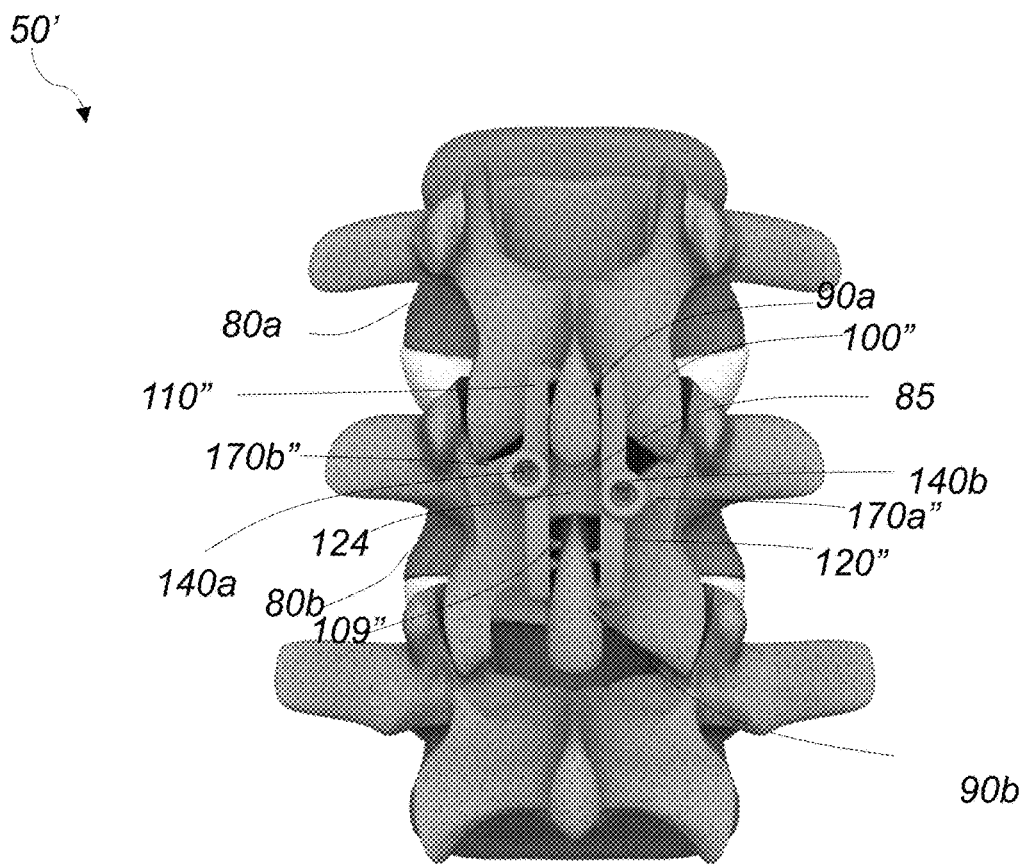
FIG. 3A is a perspective view of another embodiment of an interspinous fixation implant assembly, used to secure two adjacent vertebrae.
Figure 3B:
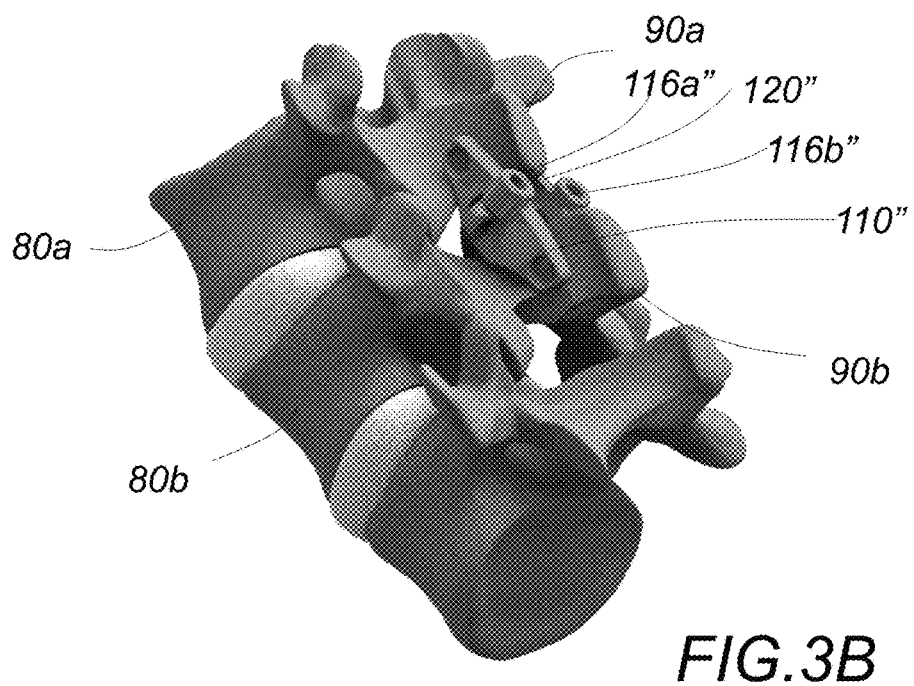
FIG. 3B is perspective side view of the interspinous fixation implant assembly of FIG. 3A.

Referring to FIG. 2A and FIG. 2B, in one embodiment, a spinous process fixation implant assembly 50 includes a spinous process fixation implant 100 and an interspinous spacer implant 200. The spinous process fixation implant 100 includes elongated first and second components 110, 120, that are arranged opposite and parallel to each other. First and second spinous processes 90a, 90b of first and second adjacent vertebrae 80a, 80b are clamped between the first and second components 110, 120, respectively, and are separated by post components 170a, 170b of the assembled implant 100 and by the interspinous spacer implant 200, as shown in FIG. 2A and FIG. 2B. In other embodiments, the spinous process fixation implant assembly 50' includes only the spinous process fixation implant 100", as shown in FIG. 3A and FIG. 3B. In this embodiment, the first and second spinous processes 90a, 90b are separated only by the post components 170a", 170b" of the assembled implant 100", as will be described below.

Figure 4A:
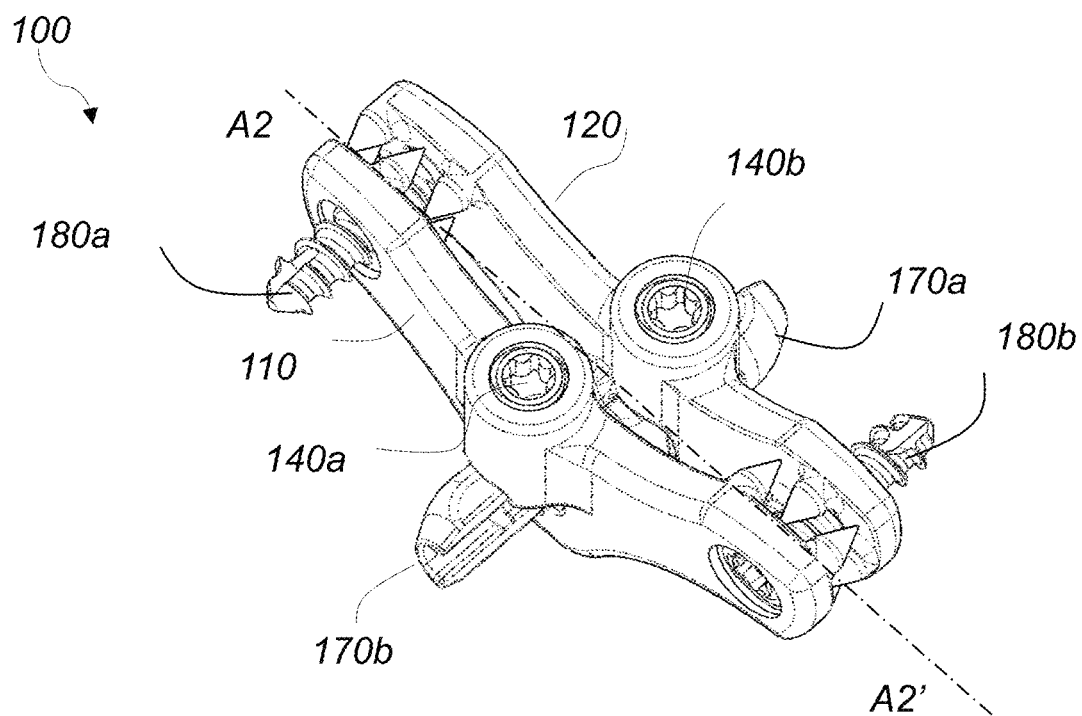
FIG. 4A is a perspective view of the interspinous fixation implant of FIG. 2A in the closed position.
Figure 4B:
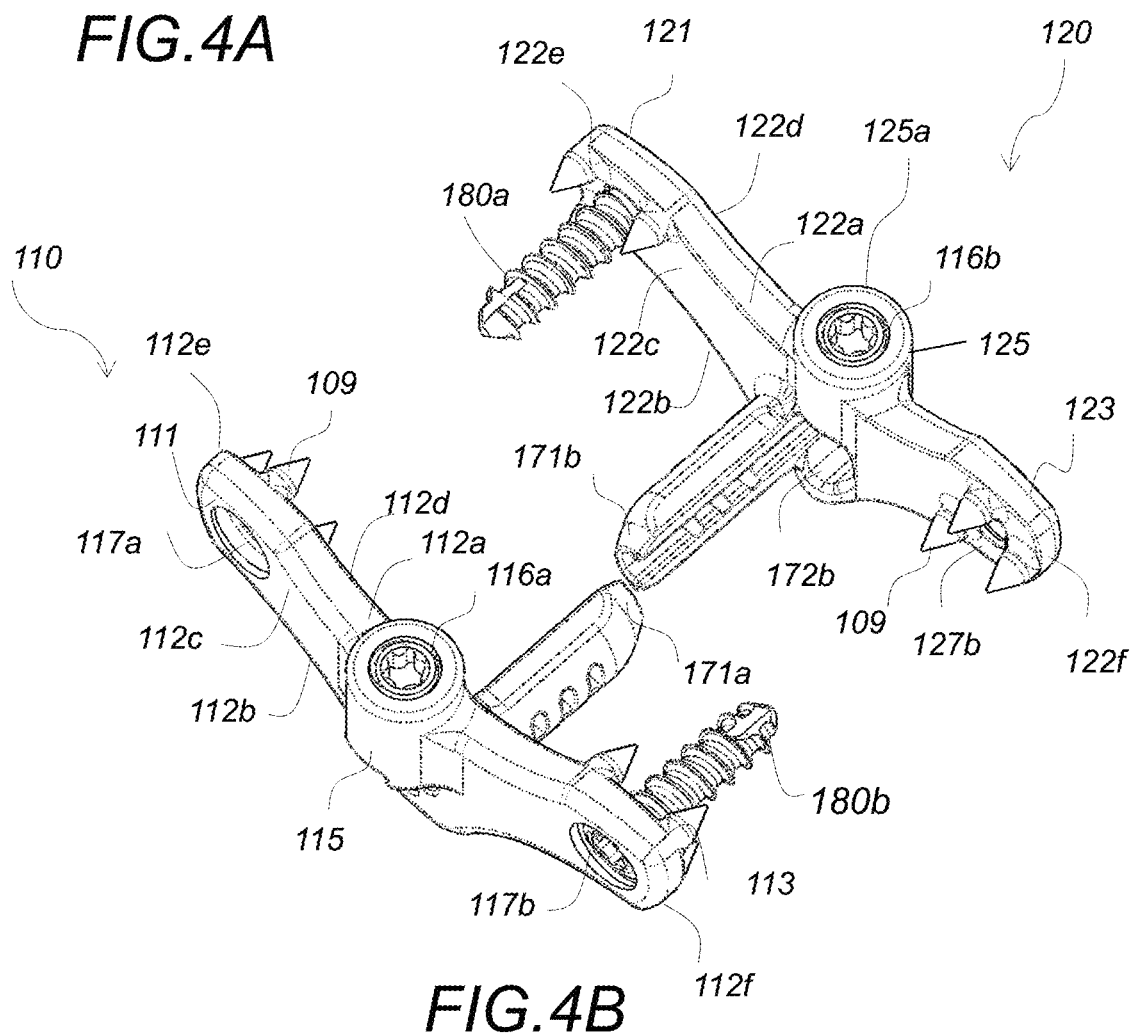
FIG. 4B is a is a partially exploded view of the interspinous fixation implant of FIG. 4A in the open position.
Figure 4C:
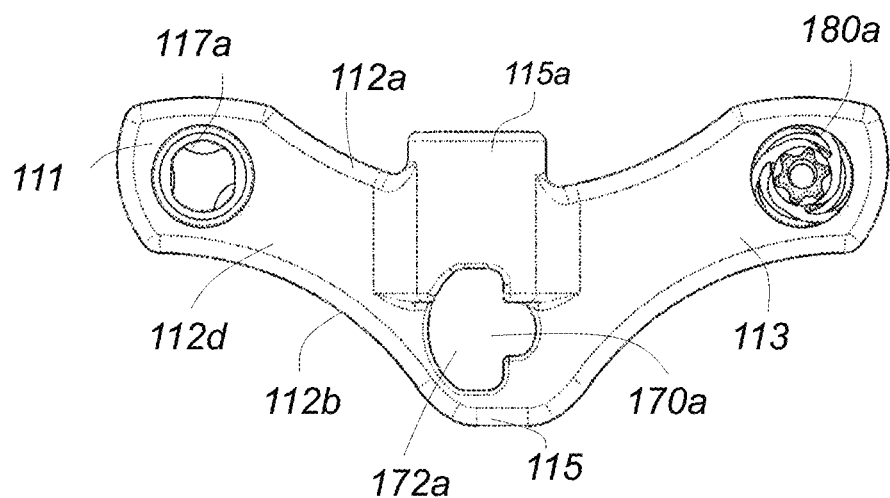
FIG. 4C is a side view of the first component of the interspinous fixation implant of FIG. 4A.

Referring to FIG. 4A-4C, spinous process fixation implant 100 includes first elongated component 110, second elongated component 120, top and bottom pins, 180a, 180b, and set screws 140a, 140b. First component 110 includes an elongated body 112 and one integral post 170a. Elongated body 112 has an essentially parallelepiped structure having parallel front and back surfaces 112a, 112b, parallel left and right side surfaces 112c, 112d and parallel top and bottom surfaces 112e, 112f, respectively. Elongated body 112 is convexly curved so that its top and bottom portions 111, 113 protrude forward relative to its middle portion 115, as shown in FIG. 4C. Middle portion 115 includes an opening 172a extending from the left surface 112c to the right surface 112d. Top portion 111 includes teeth 109 protruding from the top of right surface 112d. Bottom portion 113 also includes teeth 109 protruding from the bottom of right surface 112d. Opening 172a has a semi-circular cross-section and is dimensioned to be slightly larger than or equal to the dimensions of post 170b of component 120, so that post 170b can pass through it. Middle portion 115 also includes a cylindrical projection 115a having an opening 116a extending from the top surface 112a to the back surface 112b. Opening 116a receives set screw 140a and has dimensions matching the dimensions of screw 140a. Screw 140a secures the position of post 170b of the second component 120 onto post 170a of the first component 110 within opening 172a. Post 170a is integral with component 110 and has an essentially hollow semi-cylindrical structure. Post 170a extends perpendicularly to the right side surface 112d of the elongated body 112 from its middle portion 115. Post 170a is adjacent to opening 172a and is oriented so that its cross-section forms a full circle together with the semi-circular opening 172a, as shown in FIG. 4B.

Referring to FIG. 4B, second component 120 is the same as the first component 110 and is rotated 180° degrees relative to the orientation of the first component 110. Second component 120 includes an elongated body 122 and one integral post 170b. Elongated body 122 has an essentially parallelepiped structure having parallel front and back surfaces 122a, 122b, parallel left and right side surfaces 122c, 122d and parallel top and bottom surfaces 122e, 122f, respectively. Elongated body 122 is also convexly curved so that its top and bottom portions 121, 123 protrude forward relative to its middle portion 125. Middle portion 125 includes an opening 172b extending from the left surface 122c to the right surface 122d. Top portion 121 includes teeth 109 protruding from the top of right surface 122d. Bottom portion 123 also includes teeth 109 protruding from the bottom of right surface 122d. Opening 172b has a semi-circular cross-section and is dimensioned to be slightly larger than or equal to the dimensions of post 170a of component 110, so that post 170a can pass through it. Middle portion 125 also includes a cylindrical projection 125a having an opening 116b extending from the top surface 122a to the back surface 122b. Opening 116b receives set screw 140b and has dimensions matching the dimensions of screw 140a. Screw 140a secures the position of post 170a of the first component 110 onto post 170b of the second component 120 within opening 172b. Post 170b is integral with component 120 and has an essentially hollow semi-cylindrical structure 182, shown in FIG. 4F. Post 170b extends perpendicularly to the right side surface 122d of the elongated body 122 from its middle portion 125. Post 170b is adjacent to opening 172b and is oriented so that its cross-section forms a full circle together with the semi-circular opening 172b. Posts 170a, 170b have tapered front ends 171a, 171b. Tapered front ends 171a, 171b, help the insertion of the posts 170a, 170b through the interspinous area 85 and the openings 172b, 172a, respectively.

Figure 4D:
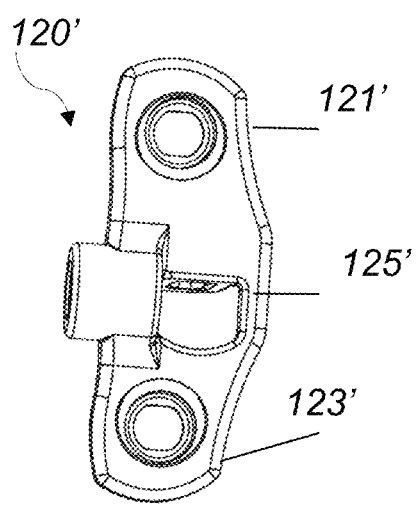
FIG. 4D is a side view of the second component of another embodiment of the interspinous fixation implant according to this invention.
Figure 4E:
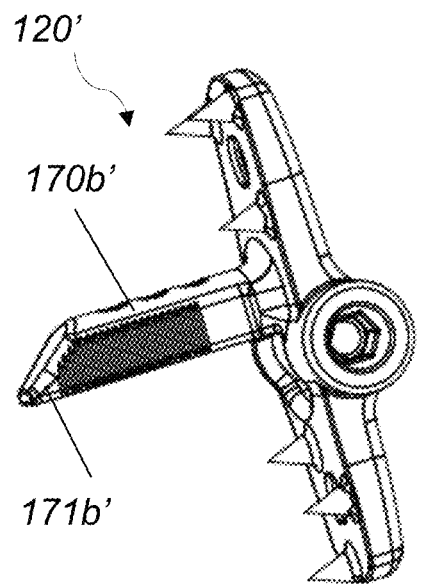
FIG. 4E is a perspective front view of the first component matching the second component of the embodiment of the interspinous fixation implant of FIG. 4D.
Figure 4F:
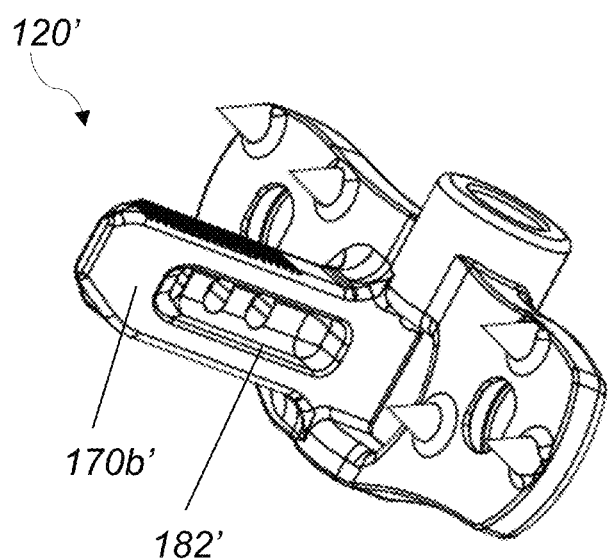
FIG. 4F is a perspective bottom view of the first component of the embodiment of the interspinous fixation implant of FIG. 4E.

In another embodiment, elongated body 122' of component 120' is not curved, and the top and bottom portions 121', 123' do not protrude relative to the middle portion 125', as shown in FIG. 4D and FIG. 4E. In this embodiment, elongated body 112' of component 110' is also not curved. In this embodiment, the front ends 171a', 171b' of posts 170a', 170b' are closed off and chamfered, as shown in FIG. 4E.

Referring to FIG. 3A and FIG. 3B, in another embodiment of the spinous process fixation implant assembly 50' spinous process fixation implant 100" includes first elongated component 110", second elongated component 120", and top set screws 140a, 140b. In this embodiment no top and bottom pins are used to secure the first and second components to the surfaces of the spinous processes.

Figure 5A:
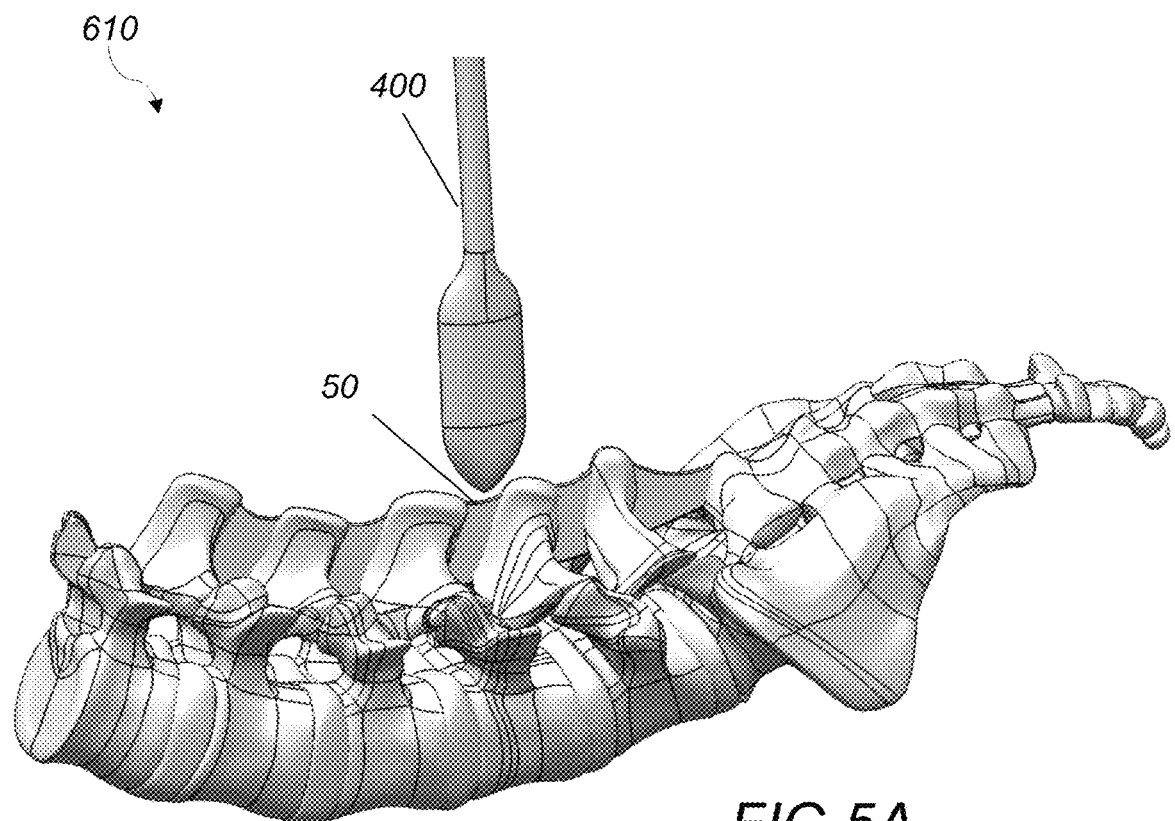
FIG. 5A and FIG. 5B depict the insertion of the decompression knife step in the decompression surgery process of this invention.
Figure 5B:
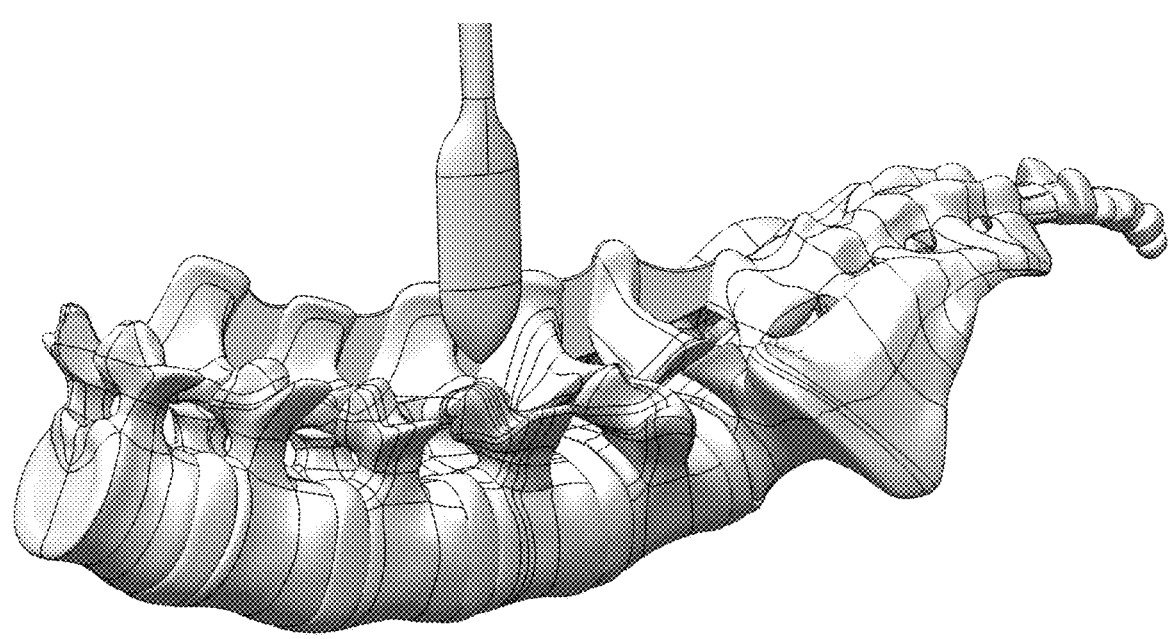
Figure 6A:
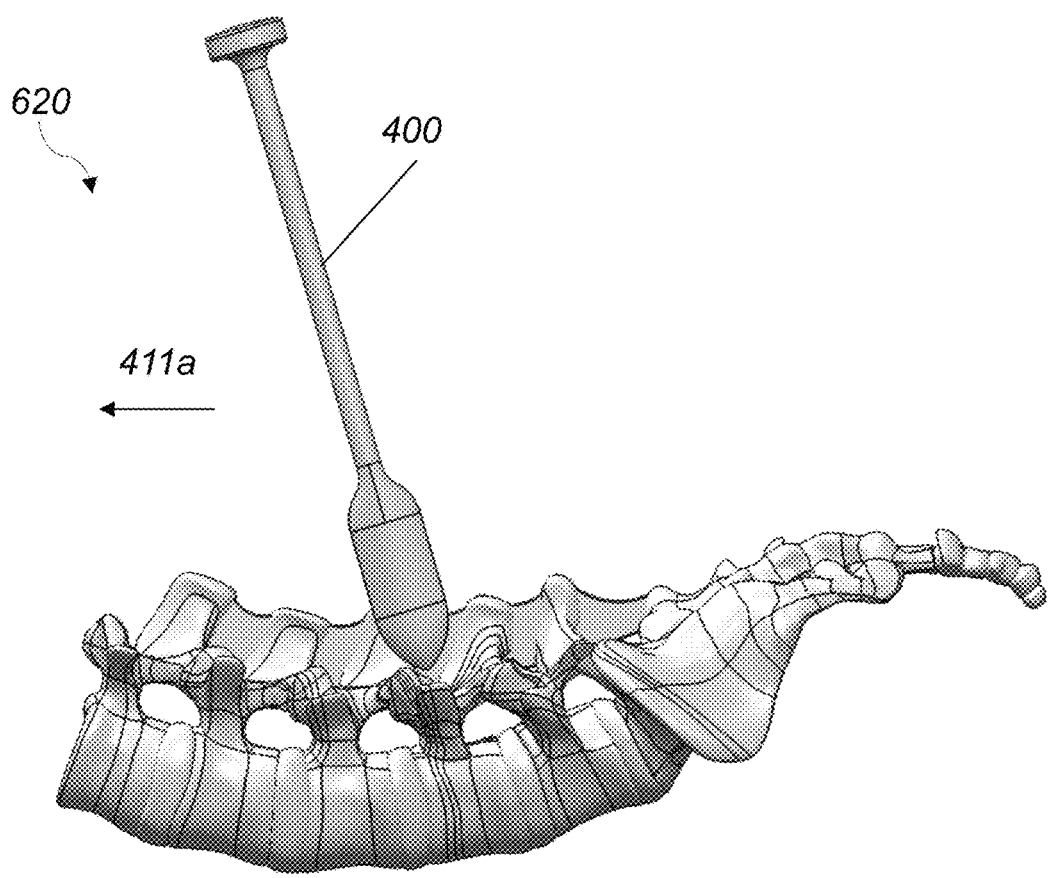
FIG. 6A and FIG. 6B depict the back and forth rocking of the decompression knife step in the decompression surgery process of this invention.
Figure 6B:
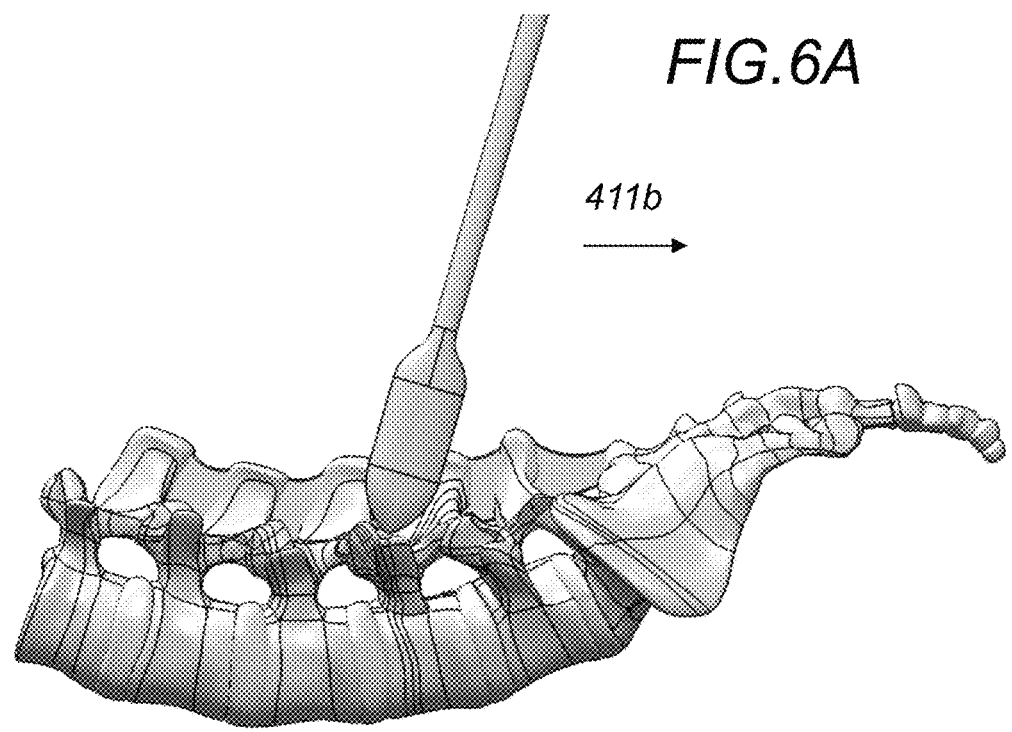
Figure 7A:
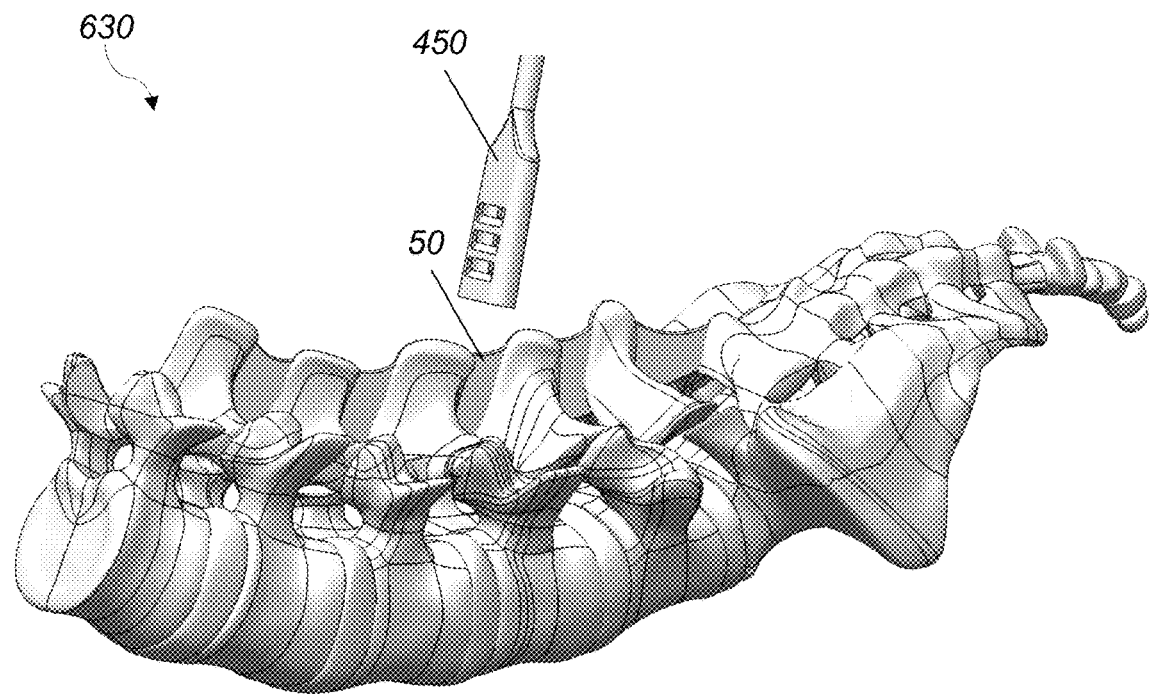
FIG. 7A and FIG. 7B depict the insertion of the broach cutter step and the cutting of the interspinous ligament step, respectively, in the decompression surgery process of this invention.
Figure 7B:
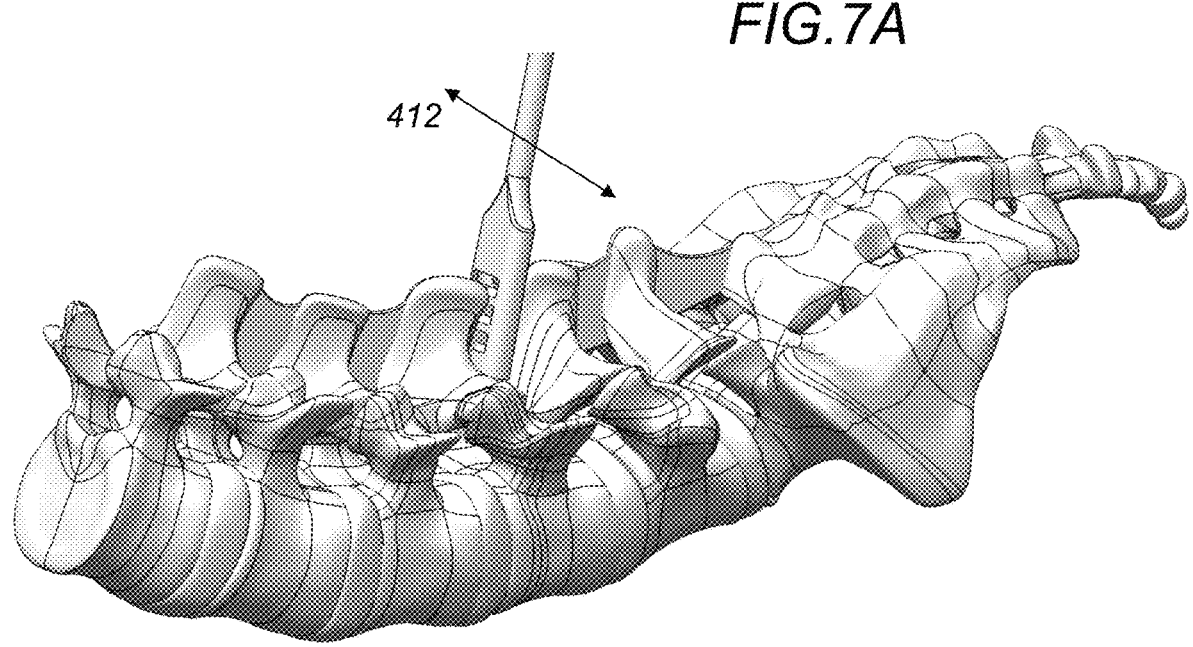
Figure 8A:
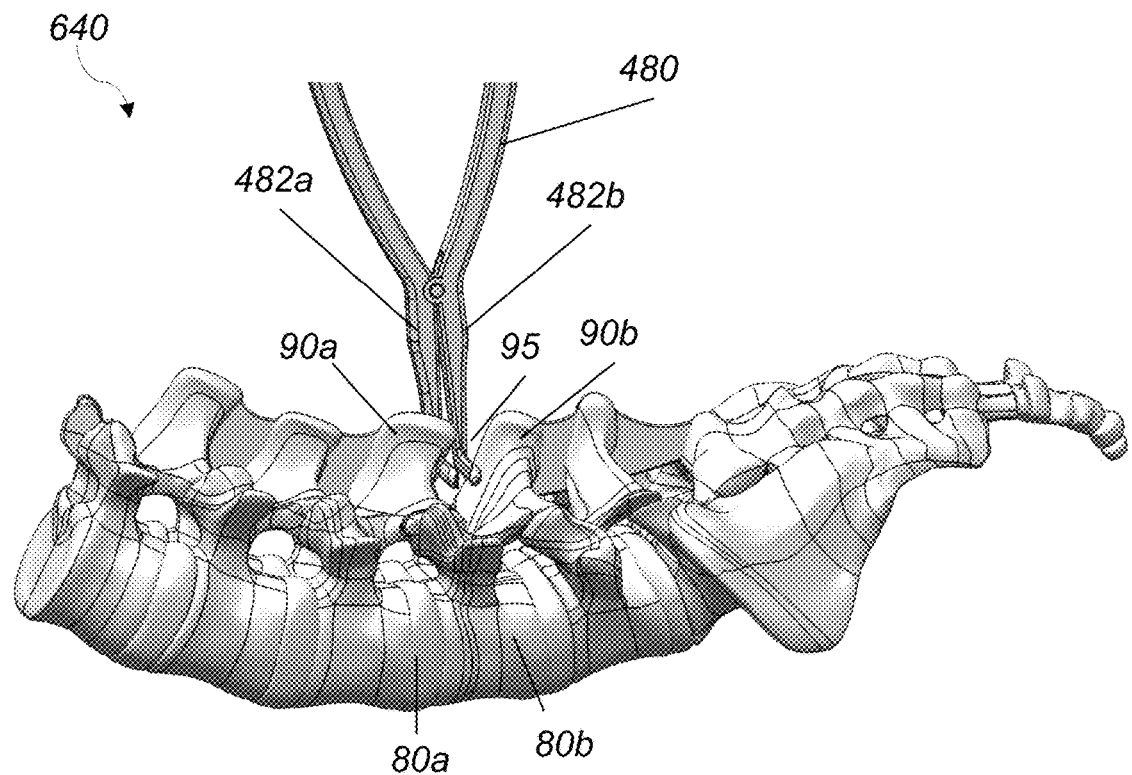
FIG. 8A and FIG. 8B depict the insertion of the sizing tool step and the measuring of the interspinous gap step, respectively, in the decompression surgery process of this invention.
Figure 8B:
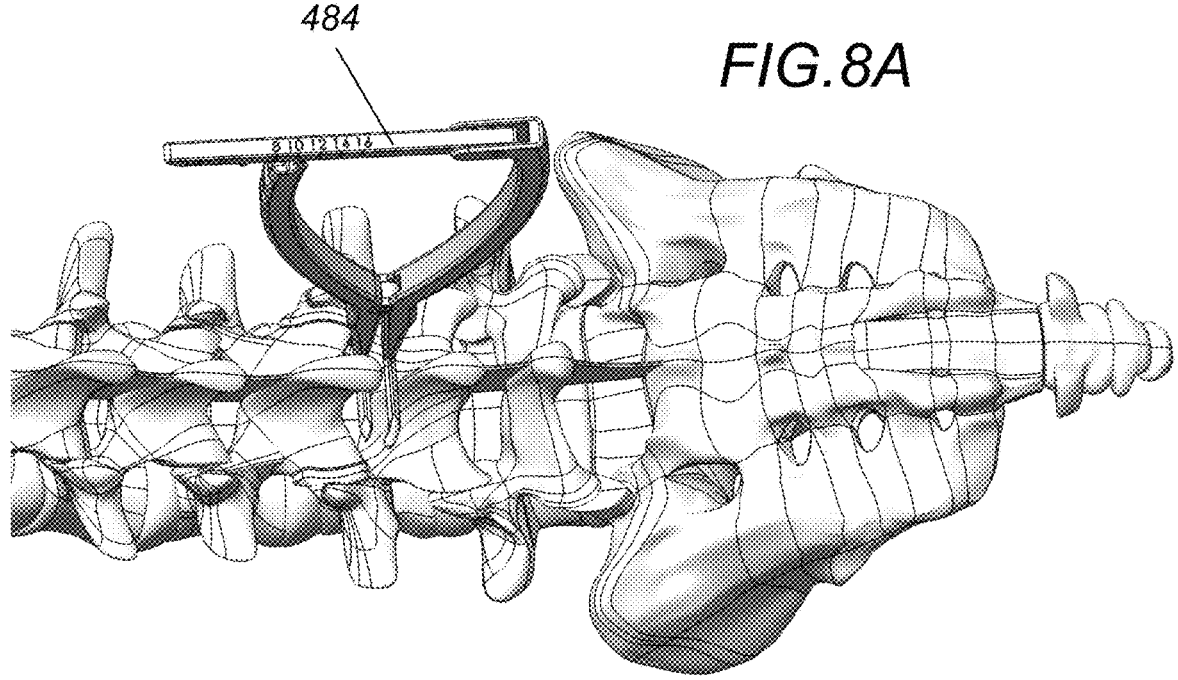
Figure 9A:
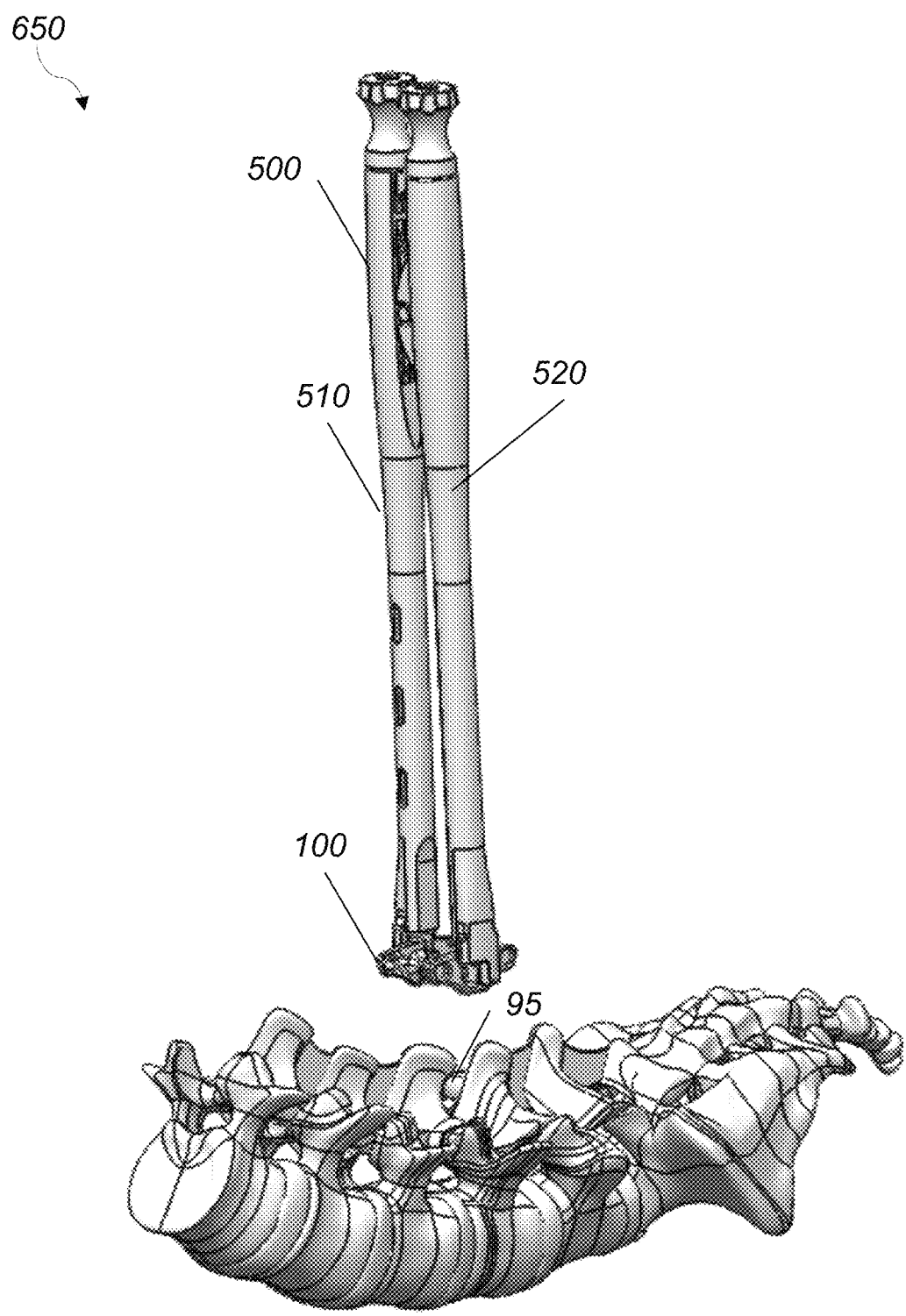
FIG. 9A, FIG. 9B and FIG. 9C depict the insertion of the implant step in the decompression surgery process of this invention.
Figure 9B:
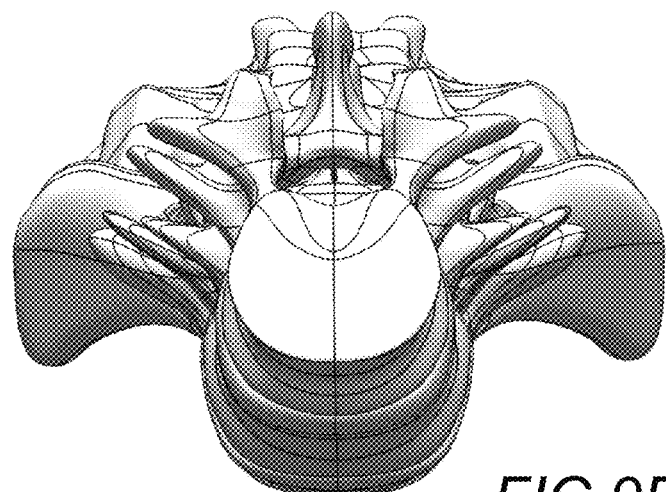
Figure 9C:
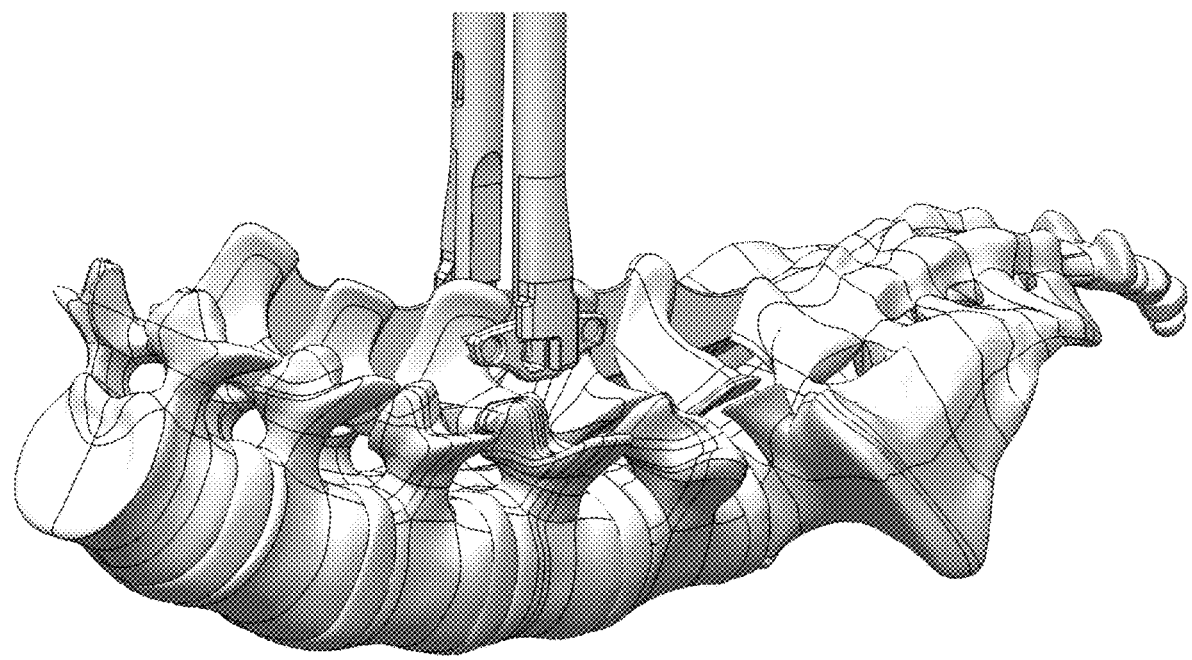
Figure 10A:
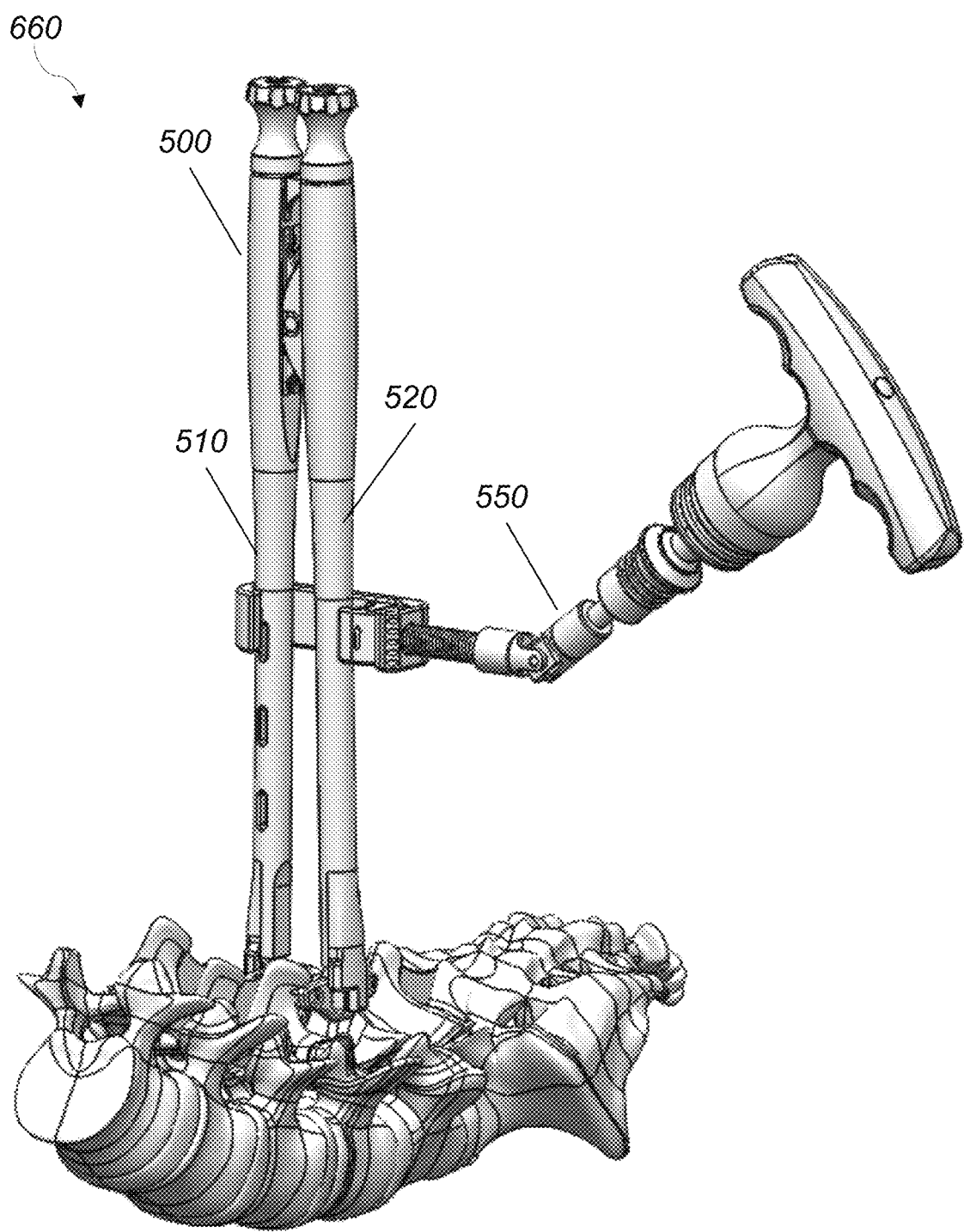
FIG. 10A, FIG. 10B, and FIG. 10C depict the compression of the implant components step, in the decompression surgery process of this invention.
Figure 10B:
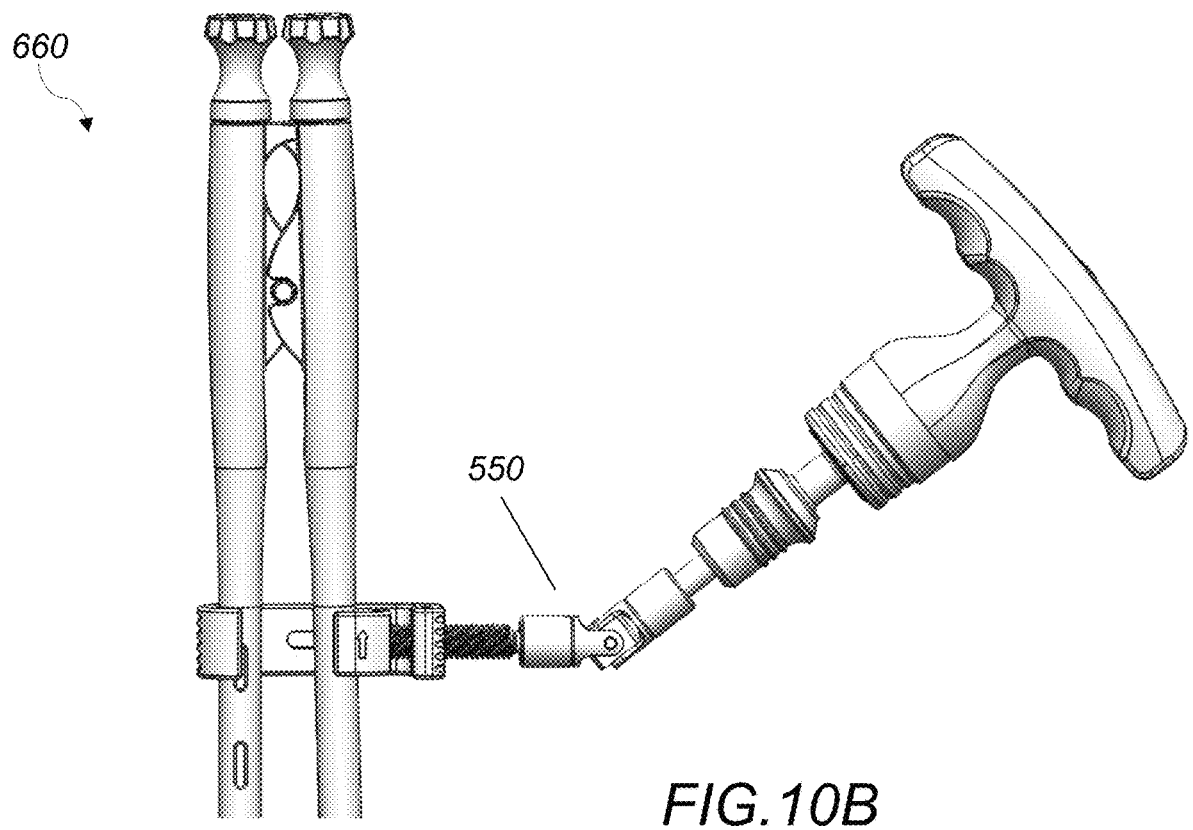
Figure 10C:
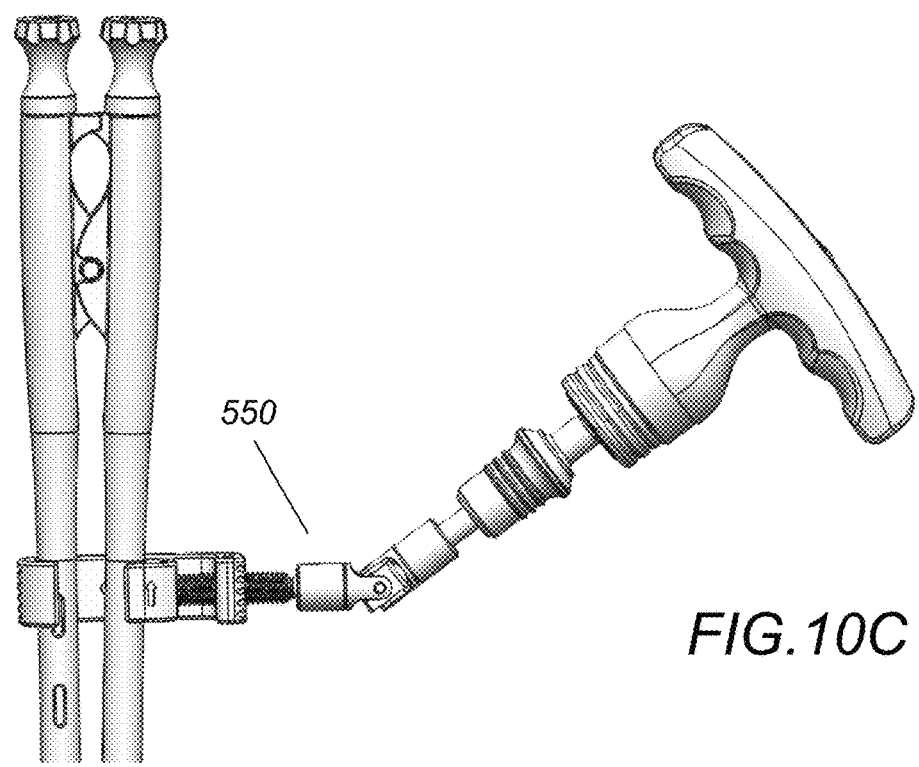

Referring to FIG. 5A-FIG. 12, the process for spinal decompression surgery 600, according to this invention includes the following steps. After exposure of the vertebras 30 in area A, a decompression knife 400 is inserted into the diseased tissue areas 50 of the vertebras, as shown in FIG. 5A-FIG. 5B (610). The decompression knife 400 is used to cut the fascia tissue 50 and separate the tissue from the bone. The decompression knife 400 is designed to function also as a cauterizing tool in order to prevent bleeding. As will be described below, decompression knife 400 includes a conducting edge 409 that is used to conduct electrical charge to the cutting site. The decompression knife 400 is also rocked back and forth along directions 411b and 411a, respectively, in order to facilitate complete separation of all soft tissue 50 from the bone, as shown in FIG. 6A-FIG. 6B (620). Next, a broach cutter 450 is inserted into the tissue area 50 of the vertebras 30 to cut the interspinous ligament along direction 412 and to remove soft tissue from the bone, as shown in FIG. 7A-FIG. 7B (630). As will be described below, broach 450 includes a sharp leading edge 457 and superior and inferior cutting edges 458, 459, in order to remove and clean all tissue away from the bone and to form a gap 95 between the spinous processes 90a, 90b and laminas of the adjacent vertebras 80a, 80b. Next, a sizing tool 480 is inserted in the opened gap 95 between the two adjacent vertebras and the gap size is measured, as shown in FIG. 8A-FIG. 8B (640). The sizing tool 480 includes two pivoting components 482a, 482b that expand and spread to measure the size of the gap 95 and thus determine the size of the appropriate implant. The sizing tool 480 also includes a size indicator 484 at the proximal end of the pivoting components 482a, 482b. Next, the implant 100 is inserted in the gap 95 with the inserter tool 500, as shown in FIG. 9A-FIG. 9C (650). Inserter tool 500 includes two elongated tubular components 510, 520 that are designed to engage the top of set screws 140a, 140b within openings 116a, 116b of the cylindrical projection 115a, 115b of implant components 110, 120, respectively, and to position and impact the implant 100 into place 95, as will be described below. Next, the implant components 110, 120 are compressed onto the sides of the adjacent spinous processes 90a, 90b, by engaging and compressing the elongated components 510, 520 of the inserter tool 500 with a compressor tool 550, as shown in FIG. 10A-FIG. 10C (660). Finally, the implant components 110, 120 are attached and locked onto the sides of the adjacent spinous processes 90a, 90b by driving screws 140a, 140b into openings with a locking driver 580, as shown in FIG. 11A-FIG. 11C (670).

Figure 13A:
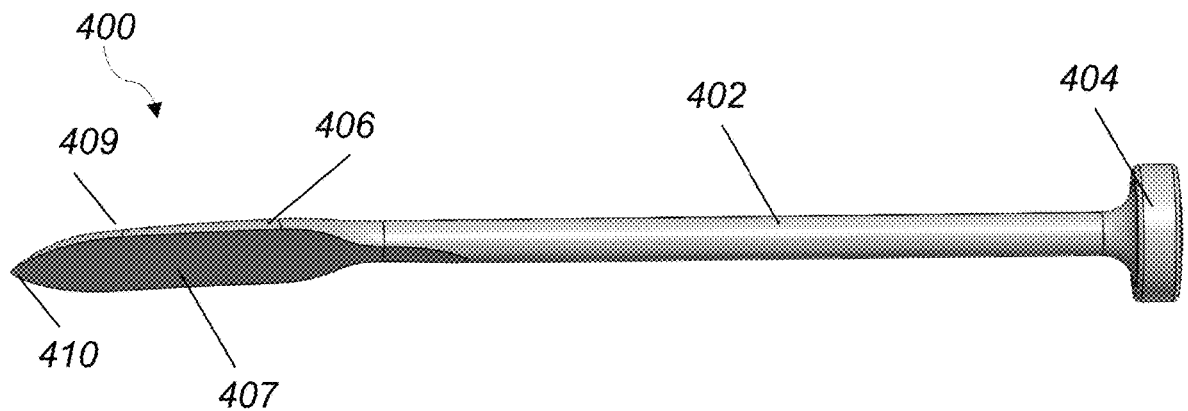
FIG. 13A depicts a side perspective view of the decompression knife of this invention.
Figure 13B:
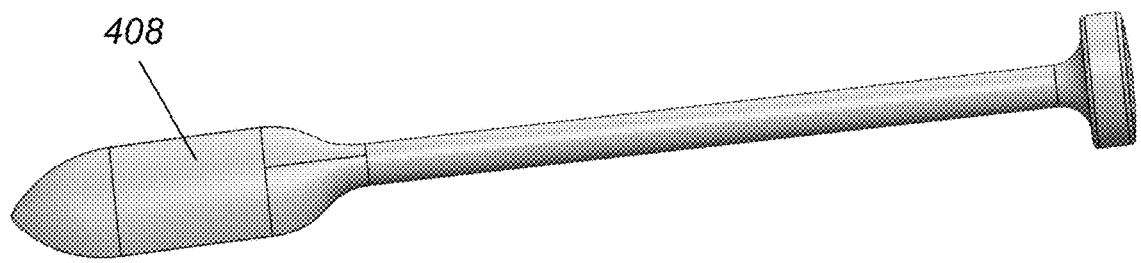
FIG. 13B depicts a back perspective view of the decompression knife of this invention.
Figure 13C:
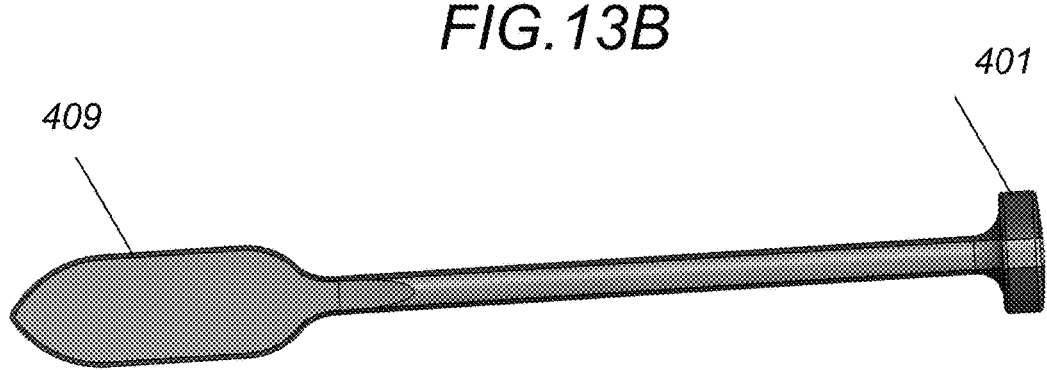
FIG. 13C depicts a front perspective view of the decompression knife of this invention.

Referring to FIG. 13A-FIG. 13C, decompression knife 400 includes an elongated shaft 402, having an elongated spade shaped distal end 406 and a handle 404 at the proximal end. The spade shaped distal end 406 has a concave inner surface 407, a convex outer surface 408 and a cutting edge 409 terminating to a sharp point 410. Sharp point 410 and cutting edge 409 are used to pierce the fascia tissue and separate the soft tissues from the bone. In one embodiment, spade 406 is made of an insulating material and cutting edge 409 is made of an electrically conducting material. In this embodiment, cutting edge 406 is connected to a power source 401 and is used to cauterize while cutting in order to prevent excessive bleeding. In one example, spade 406 is 12 mm-26 mm wide, 20 mm-150 mm long and is made of polymeric insulating materials, while the conducting cutting edge 409 is made of electrically conductive materials. Shaft 402 has a length in the range of 50 mm-150 mm and is made of stainless steel or polymeric materials. Handle 404 may be a truncated cylinder, semi-spherical, spherical or ring shaped and is made of stainless steel or polymeric materials.

Figure 14A:
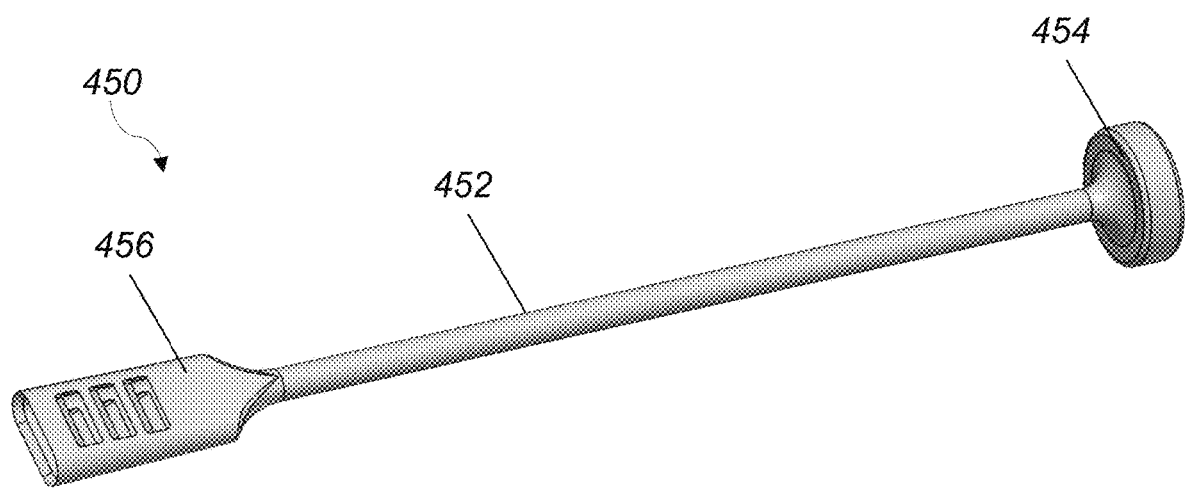
FIG. 14A depicts a front perspective view of the cutting broach of this invention.
Figure 14B:
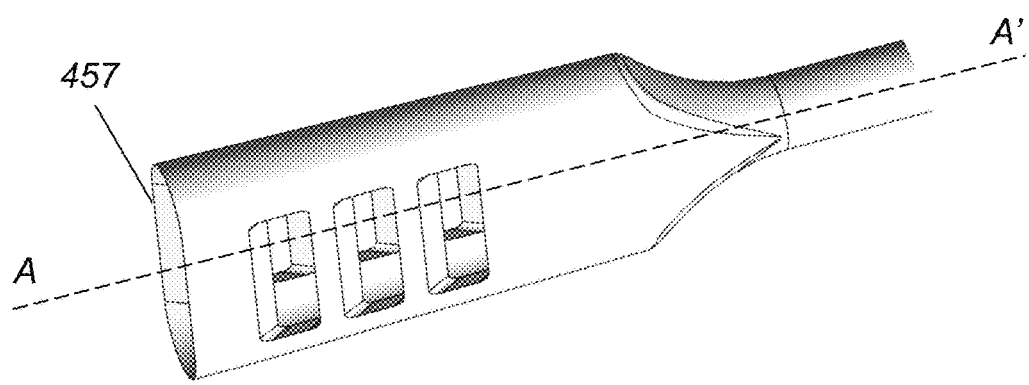
FIG. 14B depicts the cutting portion of the broach of FIG. 14A.
Figure 14C:
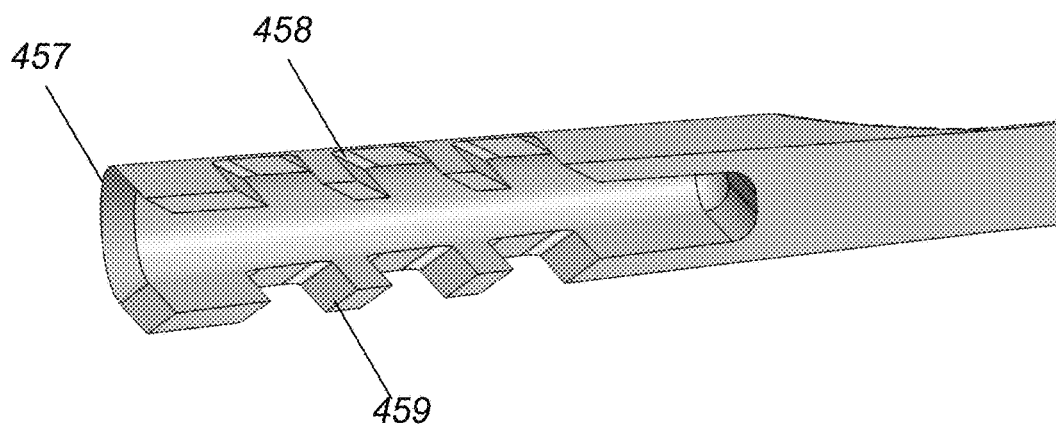
FIG. 14C depicts a cross-sectional view of the cutting portion of the broach of FIG. 14A along axis AA.

Referring to FIG. 14A-FIG. 14C, cutting broach 450 includes an elongated shaft 452, having a cutting blade 456 at the distal end and a handle 454 at the proximal end. Cutting blade 456 is a hollow parallelepiped, has a sharp cutting leading edge 457, a superior surface with cutting edges 458 and an inferior surface with cutting edges 459. Sharp leading edge 457 is used to cut the interspinous ligament and separate soft tissues from the bone. Surface cutting edges 458, 459 are used to further separate soft tissues from the bone. In one example cutting blade 456 is 12 mm-26 mm wide, 20 mm-150 mm long, has a height in the range of 6 mm-18 mm, and is made of stainless steel. Shaft 452 has a length in the range of 50 mm-150 mm and is made of stainless steel or polymeric materials. Handle 454 may be a truncated cylinder, semi-spherical, spherical or ring shaped and is made of stainless steel or polymeric materials.

Figure 11A:
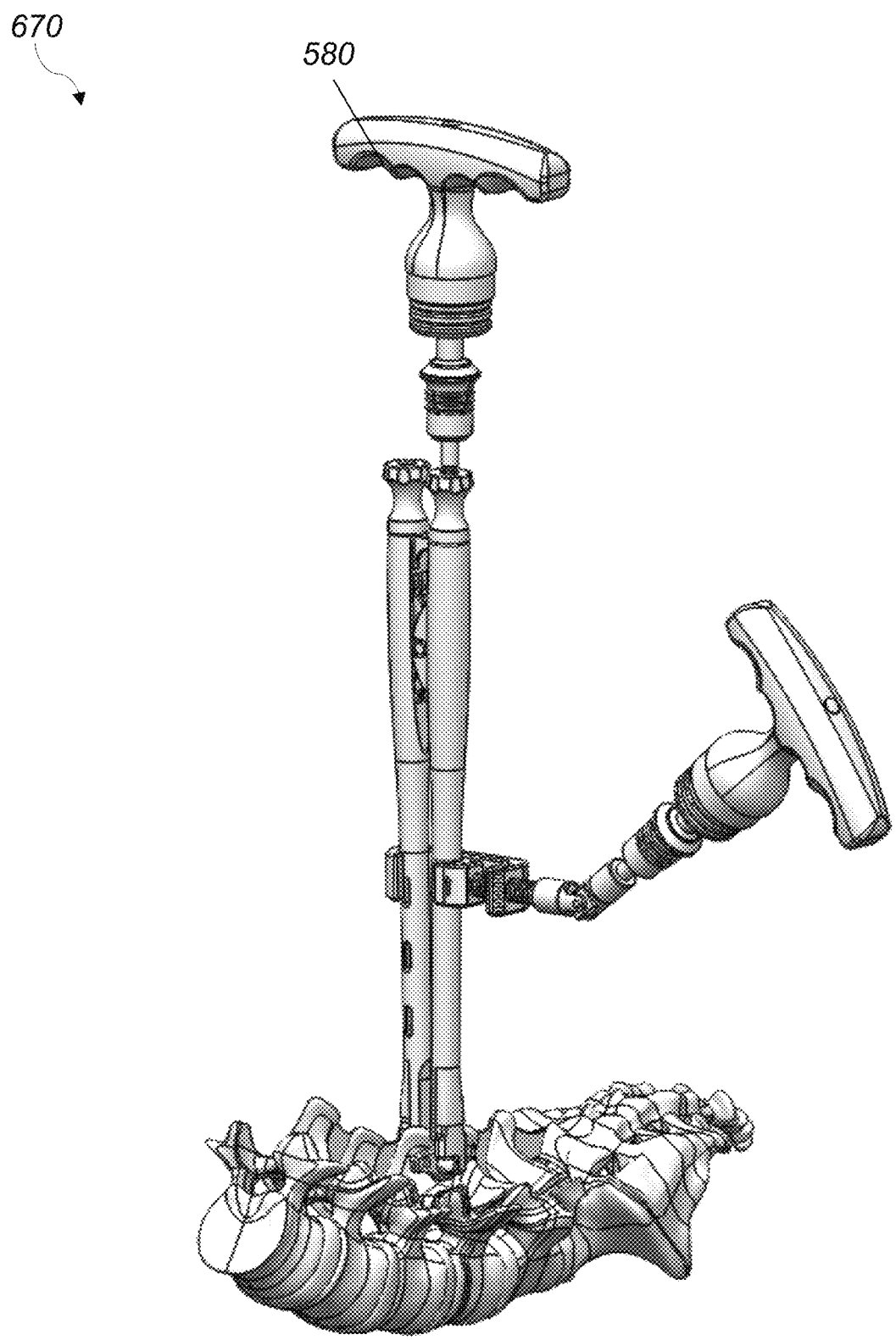
FIG. 11A, FIG. 11B, and FIG. 11C depict the locking of the implant components step, in the decompression surgery process of this invention.
Figure 11B:
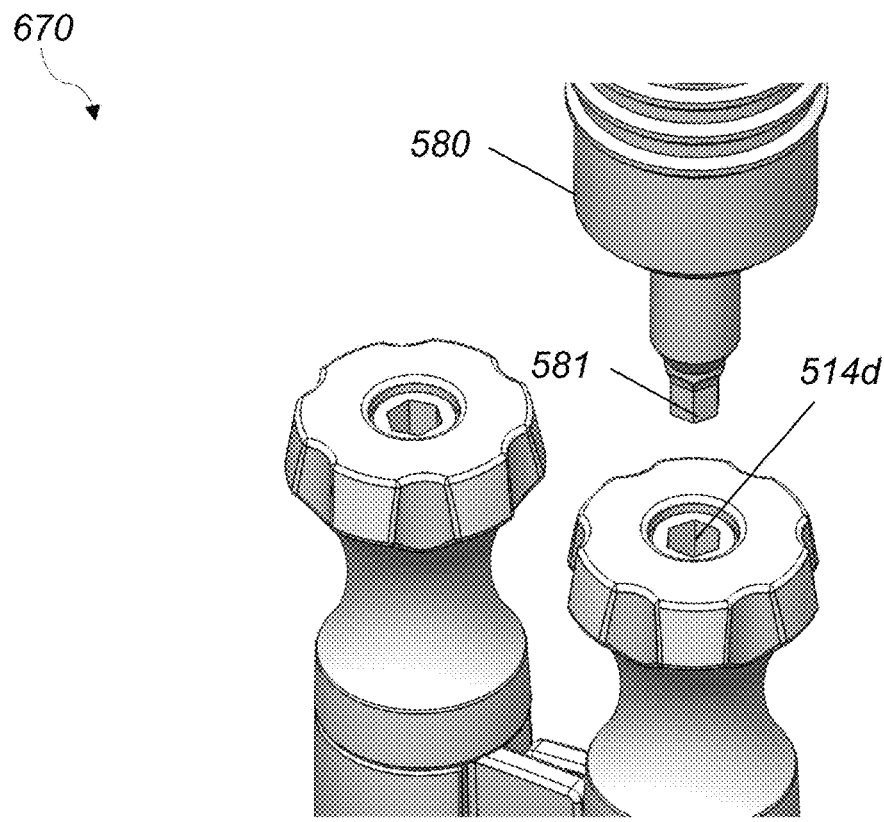
Figure 11C:
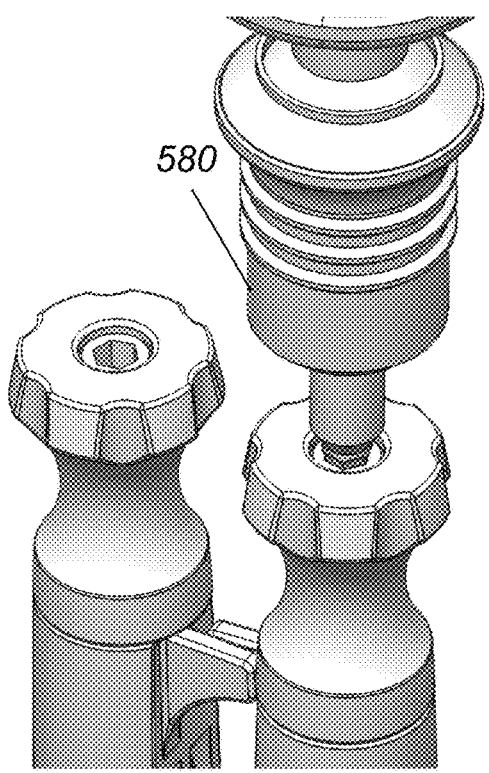
Figure 12:
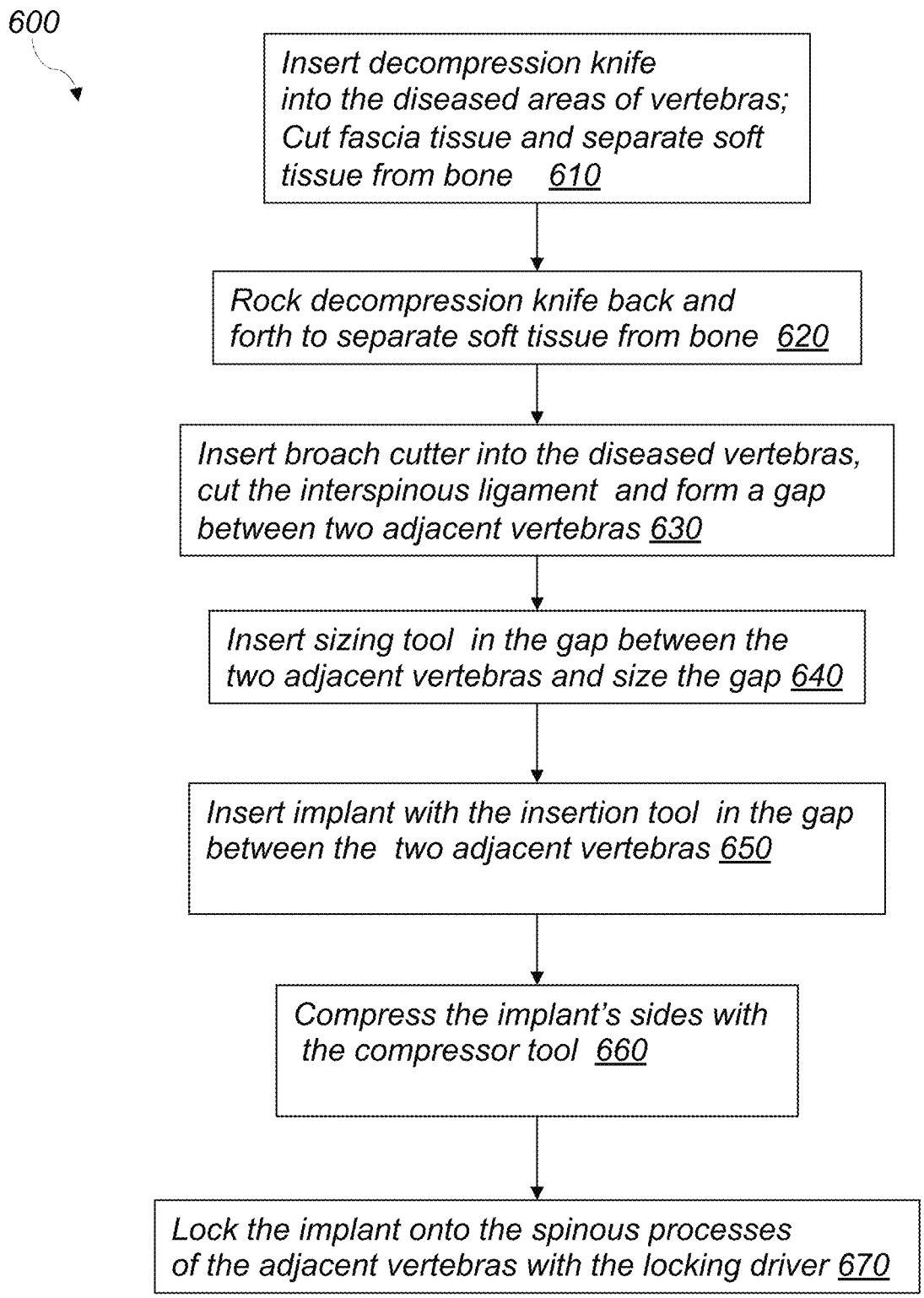
FIG. 12 depicts a block diagram of the decompression surgery process of this invention.
Figure 15A:
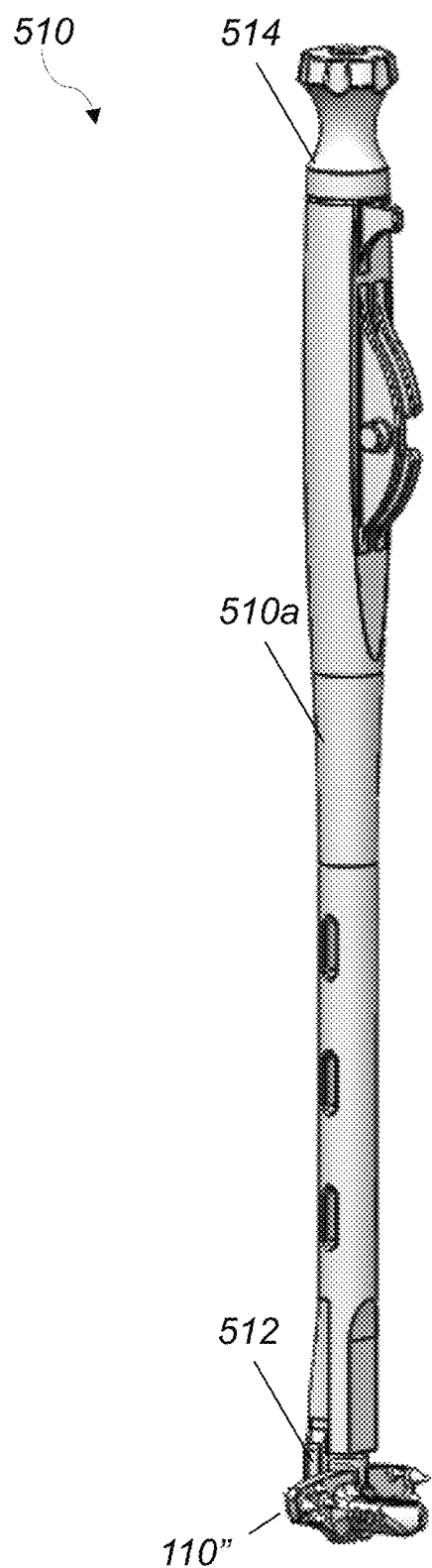
FIG. 15A depicts a perspective view of one of the two components of the inserter of FIG. 9A with one of the implant components of the embodiment of FIG. 3A attached.
Figure 15D:
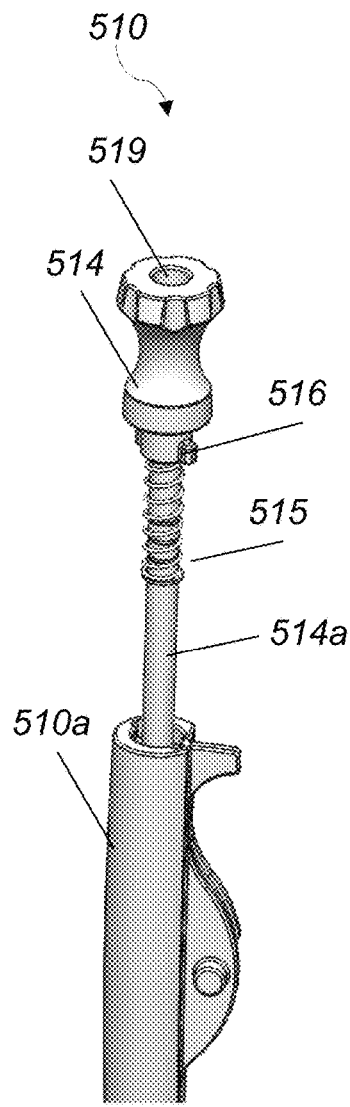
FIG. 15D depicts a perspective view of the inner stylet component of the inserter component of FIG. 15A.
Figure 15E:
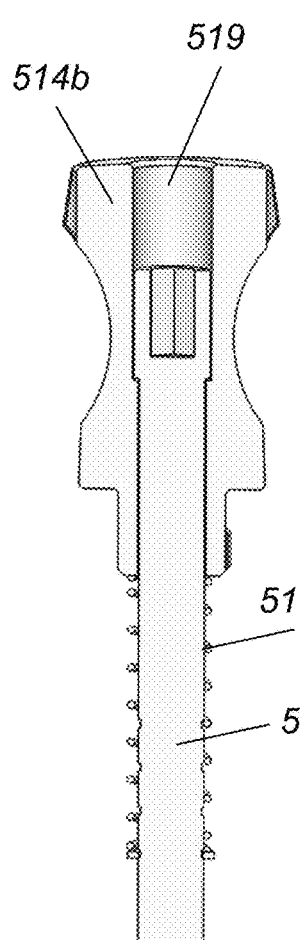
FIG. 15E depicts a cross-sectional view of the inner stylet component of the inserter component of FIG. 15A.
Figure 15F:
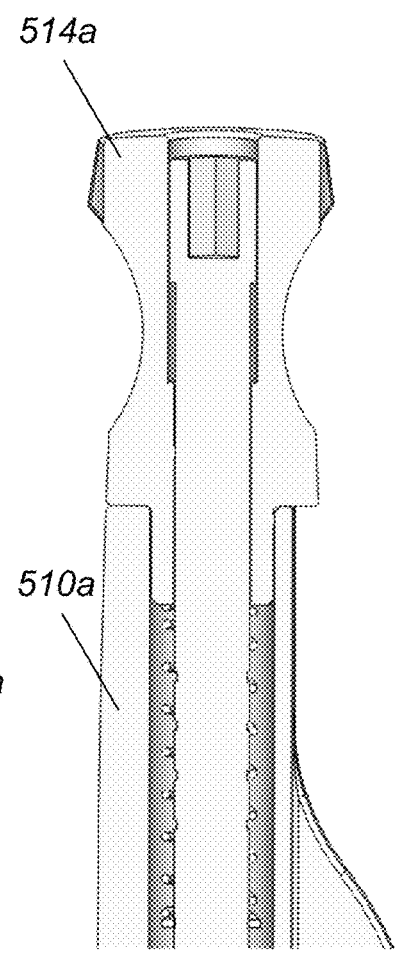
FIG. 15F depicts a cross-sectional view of the inserted inner stylet component of FIG. 16E within the inserter component of FIG. 15A.
Figure 15G:
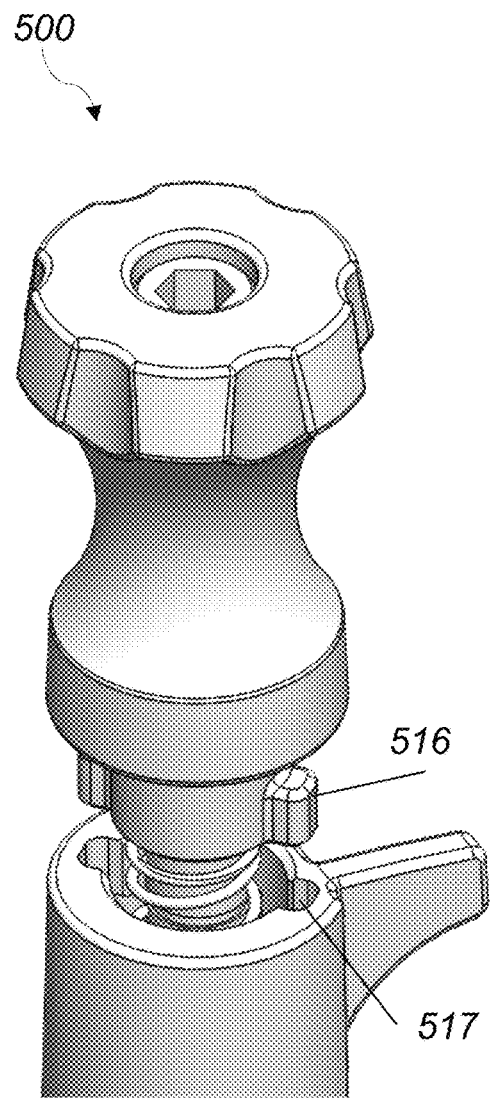
FIG. 15G depicts an enlarged view of the proximal end of the inner stylet component of the inserter component of FIG. 15A.
Figure 15H:
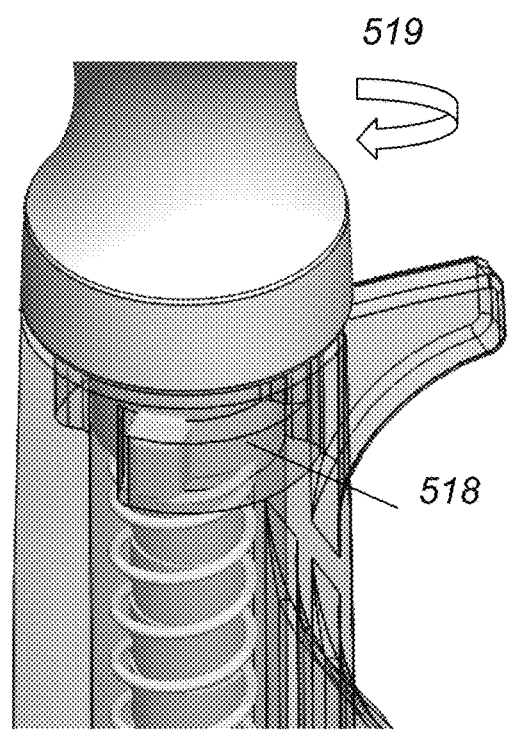
FIG. 15H depicts a transparent view of a portion of the engaged inner stylet component within the inserter component of FIG. 15A.
Figures 15I, 15J, 15K:
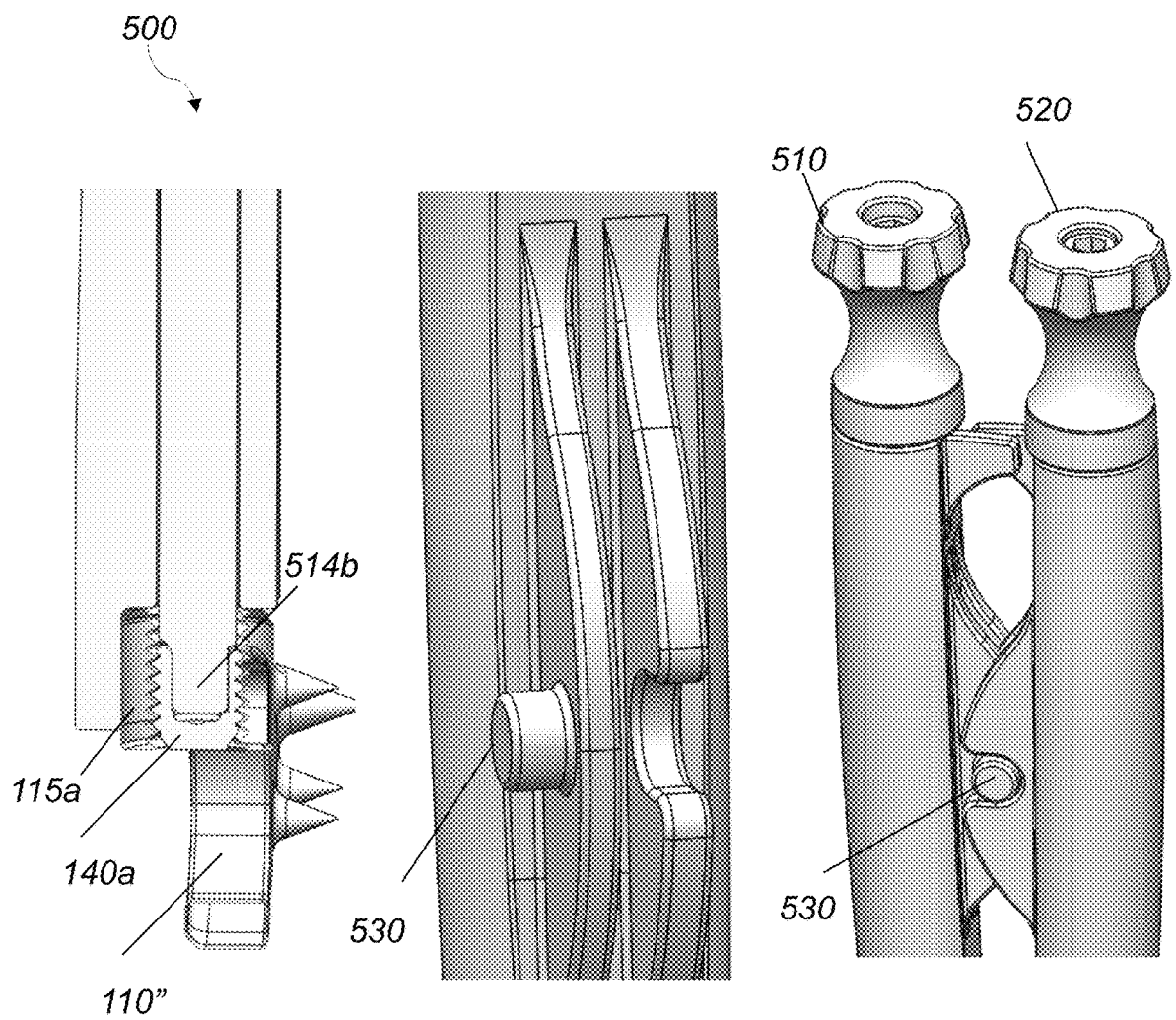
FIG. 15I depicts a side cross-sectional view of the distal end of the inserter component of FIG. 15A.
FIG. 15J depicts an enlarged view of the pivot pin of the inserter component of FIG. 15A.
FIG. 15K depicts the coupled proximal ends of the two inserter components of the inserter of FIG. 9A.

Referring to FIG. 9 and FIG. 15A-FIG. 15H, inserter 500 includes two inserter components 510, 520. Inserter component 510 includes an elongated outer tubular component 510a, and a stylet 514 that slides within the tubular component 510a. The tubular component 510a has a cutout 511 at the distal end 512. Cutout 511 is shaped and dimensioned to laterally engage the cylindrical projection 115a of the implant component 110", thereby engaging the implant component, as shown in FIG. 15B and FIG. 15C. The stylet 514 is used to lock the engaged implant component 110" onto the distal end 512 of the elongated tubular component 510a, as will be described below. Stylet 514 includes an elongated shaft 514a, a spring 515 surrounding the elongated shaft 514a, a distal end 514b and a proximal end 514c. The distal end 514b has a cross-sectional geometry matching the geometry of the top opening in the set screw 140a of the implant component 110", as shown in FIG. 15I. The proximal end 514c has a top opening 514d with a cross-sectional geometry that matches the cross-sectional geometry of the tip 581 of the locking tool 580, as shown in FIG. 11B and FIG. 11C. In operation, stylet 514 is inserted into the tubular component 510a, is aligned so that collar protrusions 516 fit into cut openings 517 formed on the inner sides of the tubular component 510a and pressed down so that the distal end 514b engages the top opening of the set screw 140a of the implant component 110", as shown in FIG. 15G-FIG. 15I. Pressing down of the stylet 514 into the tubular component 510a compresses the spring 515 and a subsequent quarter turn rotation 519 of the stylet 514 moves collar protrusions 516 into undercuts 518 formed in the inner sides of the tubular component 510a, thereby keeping spring 515 under tension and locking the stylet 514 within the tubular component 510a and keeping constant force onto the implant component 110", thereby creating a robust connection between the inserter component 510 and the implant component 110", as shown in FIG. 15G and FIG. 15H. Inserter component 520 has a 180° degrees rotated image structure of the inserter component 510. Inserter components 510, 520 engage each other via the pivot pins 530. The pivoting of inserter components 510, 520, provides rotational flexibility in the positioning of the implant components 110", 120" around the surfaces of the spinous processes. Inserter 500 is also used to impact the implant 100" into place so that surfaces 112b and 122d interface with the laminas.

Figure 16A:
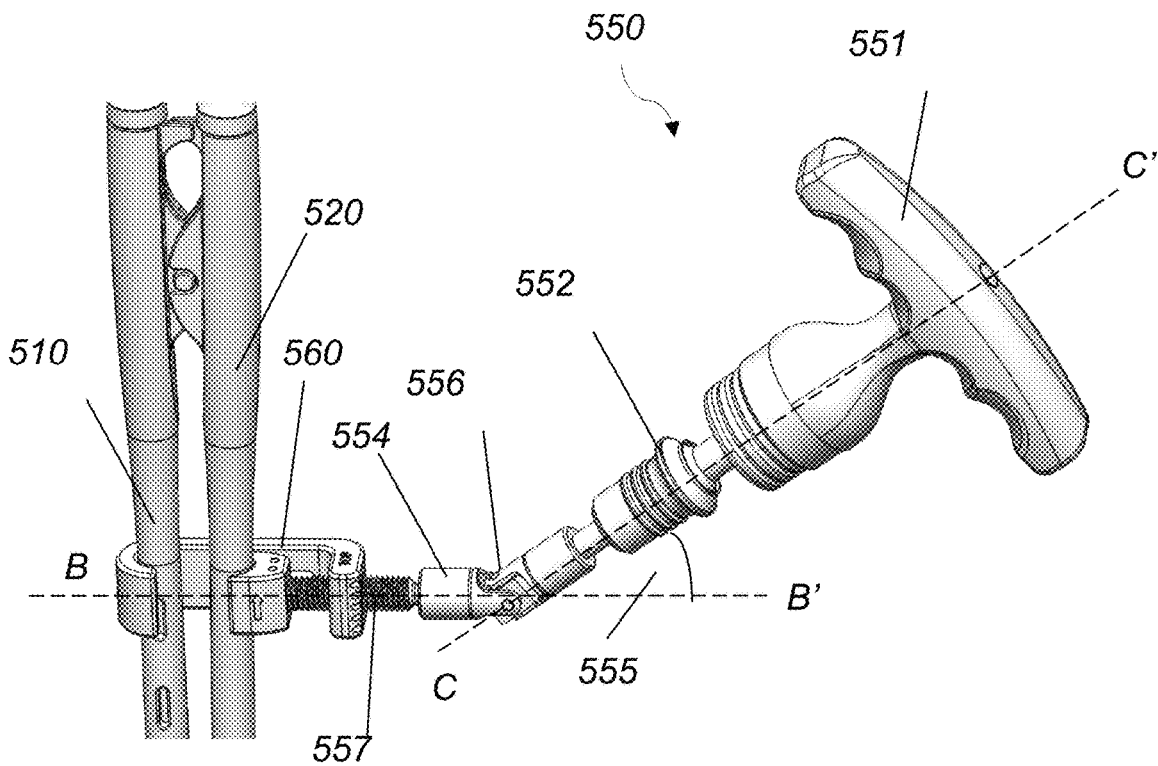
FIG. 16A depicts the central compressor component of FIG. 10A engaging the two components of the inserter component of FIG. 9A.
Figure 16B:
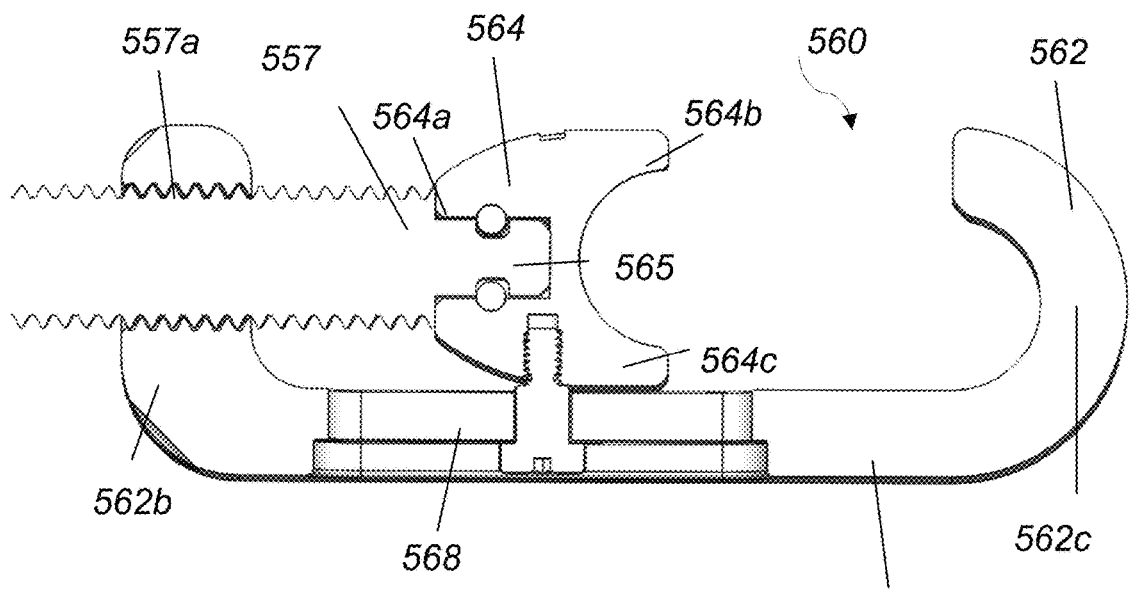
FIG. 16B depicts a cross-sectional view of the jaw component of the central compressor component of FIG. 10A, along axis BB'.
Figure 16C:
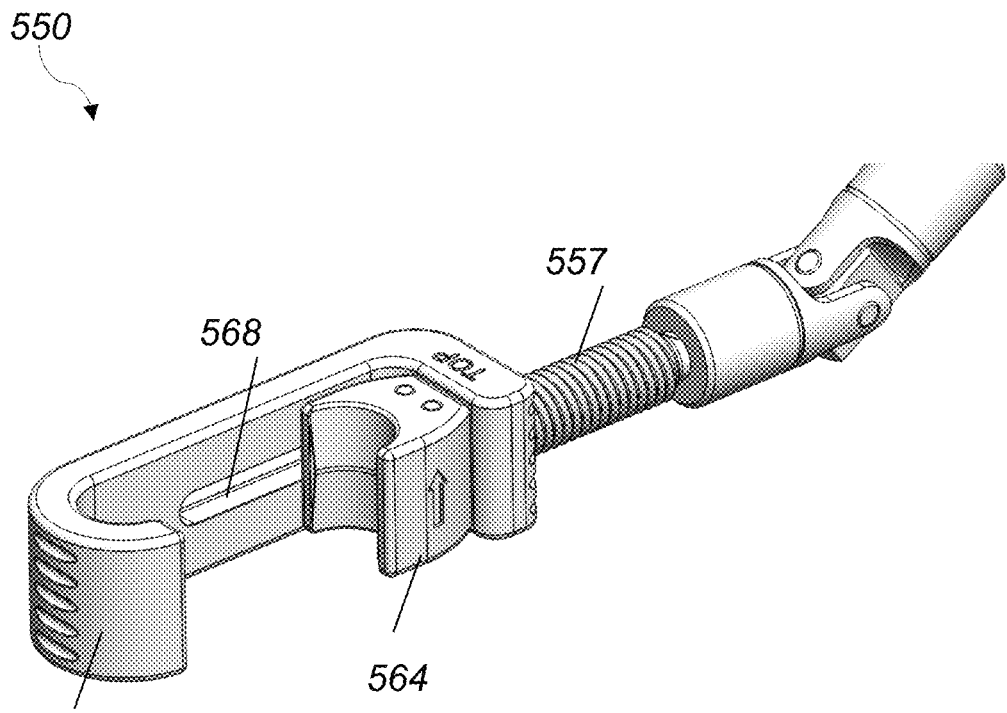
FIG. 16C depicts the jaw component of the central compressor component of FIG. 10A in the open position.
Figure 16D:
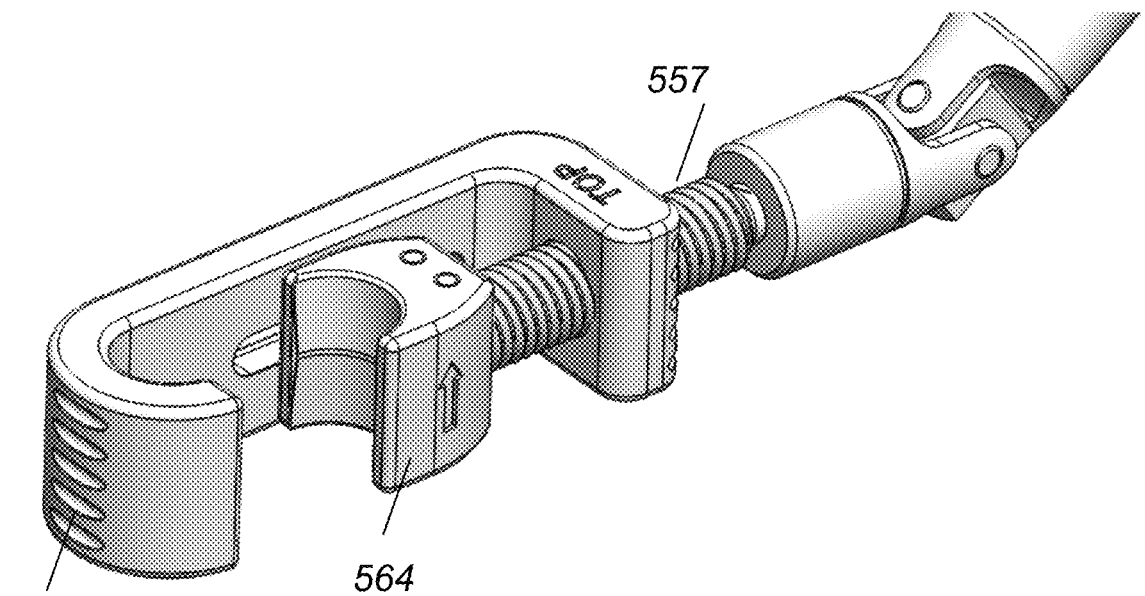
FIG. 16D depicts the jaw component of the central compressor component of FIG. 10A in the partially closed position.

Referring to FIG. 16A-FIG. 16D and FIG. 10A-FIG. 11A, compressor tool 550 includes first and second elongated components 552, 554 and a jaw component 560. First and second elongated components 552, 554 are linked together via a multiaxially rotatable pivot link 556. Pivot link 556 allows rotational motion of component 554 around axis BB' by rotating the pivotably connected component 552 around axis CC', which forms a pivot angle 555 with axis BB". Elongated component 552 has a handle 551 at the proximal end that is used for rotating the component 552 around axis CC'. Elongated component 554 has a distal portion that forms a screw 557 having outer threads 557a. Screw 557 screws into the jaw component 560. Jaw component 560 includes a fixed jaw 562 and a movable jaw 564. Movable jaw 564 is designed to slidably move within the stationary jaw 562. Fixed jaw component 562 has a U-shaped cross section with an elongated flat bottom portion 562a, a straight proximal leg 562b and a curved distal leg 562c. Movable jaw component 564 has a U-shaped cross-section with a short curved bottom 564a and straight top and bottom legs 564b, 564c. The distal end of screw 557 of the elongated component 554 engages an opening 565 formed at the curved bottom 564a of the movable jaw 564. Rotational motion of the elongated component 554 around axis CC' translates screw 557 and the movable jaw 564 along axis CC' within the stationary jaw 562. Bottom leg 564c of the movable jaw 564 is slidably attached to a slot 568 formed in the flat bottom portion 562a of the stationary jaw 562. The movable jaw 564 and the curved leg 562c of the stationary jaw 562 form a clam structure that engages and compresses the inserter components 520, 510, respectively. As shown in FIG. 16A, curved leg 562 of the stationary jaw component 562 grabs the inserter component 510 and the opposing movable jaw 564 grabs the inserter component 520. Forward motion of screw 557 moves movable jaw 564 forward and thereby closer to the opposing curved leg 562 of the stationary jaw component 562 and thereby compresses inserter components 510 and 520 together. The compression of the inserter component 510, 520, translates into compression of the implant components 110", 120" onto to the outer surfaces of the spinous processes 90a, 90b.

As was described above, the first component 110" of implant 100" is placed in contact with the left sides of top and bottom spinous process 90a, 90b of adjacent vertebrae 80a, 80b, respectively, as shown in FIG. 3A and FIG. 3B. Second component 120" of implant 100" is placed in contact with the right sides of top and bottom spinous process 90a, 90b of adjacent vertebrae 80a, 80b, respectively. Post 170a" of the first component 110" is inserted into opening 172b" of the second component 120", and post 170b" of the second component 120" is inserted into openings 172a" of the first component 110". Fully inserted posts 170a", 170b" interface with the corresponding openings 172a", 172b", and with each other to form a hollow cylindrical hub structure 124, as shown in FIG. 3A. The two components 110", 120" are pressed against the left and right of the top and bottom spinous processes 90a, 90b, respectively, and set screws 140a, 140b are screwed into openings 116a", 116b", to compress and secure the position of the two components 110', 120', respectively. Teeth 109" at the top and bottom portions of components 110", 120" penetrate into the sides of the top and bottom spinous processes 90a, 90b, respectively.

Several embodiments of the present invention have been described. Nevertheless, it will be understood that various modifications may be made without departing from the spirit and scope of the invention. Accordingly, other embodiments are within the scope of the following claims.

What is claimed is:

1. A method for inserting an interspinous spinal implant into an opened gap between first and second spinous processes of adjacent superior and inferior vertebras, respectively, comprising:
    forming an opened gap between a first spinous process of a superior vertebra and a second spinous process of an adjacent inferior vertebra by first inserting a decompression knife into diseased areas of the adjacent superior and inferior vertebras, then cutting fascia tissue, then separating soft tissue from bone by rocking the decompression knife back and forth, and then inserting a broach cutter into the diseased areas of the adjacent superior and inferior vertebras and cutting interspinous ligament between the adjacent superior and inferior vertebras;
    determining and selecting an appropriate sized and shaped interspinous spinal implant for the opened gap by inserting a sizing tool into the opened gap, and sizing the opened gap with the sizing tool;
    inserting the selected interspinous spinal implant into the opened gap with an insertion tool, wherein the interspinous spinal implant comprises a first elongated component and a second elongated component arranged parallel and opposite the first elongated component;
    compressing the first and second elongated components of the interspinous spinal implant onto first and second opposite sides of the first and second spinous processes with a compressor tool, respectively; and
    locking the interspinous spinal implant onto the first and second spinous processes of the adjacent superior and inferior vertebras with a locking driver.

2. The method of claim 1, wherein each of the first and second elongated components comprises an elongated body extending along a first direction and an integral post extending from the elongated body perpendicular to the first direction;

wherein each elongated body comprises an opening extending perpendicular to the first direction and wherein the opening is shaped and sized to receive the integral post of the opposite elongated component;

wherein each elongated body comprises a cylindrical projection having an opening configured to receive a set screw and wherein the set screw is configured to secure the position of the integral post of the first elongated component onto the integral post of the second elongated component; and wherein the integral post comprises an essentially hollow semi-cylindrical structure.

3. The method of claim 1, wherein the interspinous spinal implant further comprises top and bottom pins used to secure the first and second elongated components onto the first and second spinous processes, respectively.

4. The method of claim 1, wherein the decompression knife comprises an elongated shaft having an elongated spade at a distal end and a handle at a proximal end and wherein the elongated spade comprises a concave inner surface, a convex outer surface, and a cutting edge terminating to a sharp point.

5. The method of claim 4, wherein the elongated spade comprises an electrically insulating material and the cutting edge comprises an electrically conducting material and wherein the cutting edge is connected to a power source and is used to cauterize tissue while cutting.

6. The method of claim 1, wherein the broach cutter comprises an elongated shaft having a cutting blade at a distal end and a handle at a proximal end and wherein the cutting blade comprises a hollow parallelepiped having a sharp cutting leading edge, a superior surface with a plurality of cutting edges, and an inferior surface with a plurality of cutting edges.

7. The method of claim 1, wherein the insertion tool comprises first and second elongated inserter components and wherein each elongated inserter component comprises an elongated outer tubular component and a stylet configured to slide within the outer tubular component and wherein the outer tubular component comprises a cutout at a distal end shaped and sized to laterally engage a cylindrical projection of the first or second elongated components.

8. The method of claim 7, wherein the stylet comprises a stylet elongated shaft and a spring surrounding the stylet elongated shaft and wherein a distal end of the stylet elongated shaft has a cross-sectional geometry matching the geometry of a top opening in a set screw of the interspinous spinal implant and wherein the stylet is configured to lock the first or second elongated components onto the distal end of the tubular component, by pressing down and rotating the stylet elongated shaft.

9. The method of claim 1, wherein the compressor tool comprises first and second components and a jaw component and wherein the first and second components are linked together via a multiaxially rotatable pivot link and wherein the distal end of the second component comprises a screw that attaches to the jaw component.

10. The method of claim 9, wherein the jaw component comprises a fixed jaw and a movable jaw and wherein the movable jaw is configured to slidably move within the fixed jaw via rotational motion of the second component and wherein the fixed jaw and the movable jaw are configured to engage and compress together the first and second elongated inserter components, respectively.

11. A system for inserting an interspinous spinal implant into an opened gap between first and second spinous processes of adjacent superior and inferior vertebras, respectively, comprising:

a decompression knife used for forming an opened gap between a first spinous process of a superior vertebra and a second spinous process of an adjacent inferior vertebra by first inserting the decompression knife into diseased areas of the adjacent superior and inferior vertebras, then cutting fascia tissue, and then separating soft tissue from bone by rocking the decompression knife back and forth;

a broach cutter used for cutting interspinous ligament between the adjacent superior and inferior vertebras;

an appropriate sized and shaped interspinous spinal implant configured to be inserted into the opened gap, wherein the interspinous spinal implant comprises a first elongated component and a second elongated component arranged parallel and opposite the first elongated component;

a sizing tool for determining and selecting the appropriate sized and shaped interspinous spinal implant for the opened gap;

an insertion tool for inserting the selected interspinous spinal implant into the opened gap;

a compressor tool for compressing the first and second elongated components of the interspinous spinal implant onto first and second opposite sides of the first and second spinous processes respectively; and a locking driver for locking the interspinous spinal implant onto the first and second spinous processes of the adjacent superior and inferior vertebras.

12. The system of claim 11, wherein each of the first and second elongated components comprises an elongated body extending along a first direction and an integral post extending from the elongated body perpendicular to the first direction;

wherein each elongated body comprises an opening extending perpendicular to the first direction and wherein the opening is shaped and sized to receive the integral post of the opposite elongated component;

wherein each elongated body comprises a cylindrical projection having an opening configured to receive a set screw and wherein the set screw is configured to secure the position of the integral post of the first elongated component onto the integral post of the second elongated component; and wherein the integral post comprises an essentially hollow semi-cylindrical structure.

13. The system of claim 11, wherein the interspinous spinal implant further comprises top and bottom pins used to secure the first and second elongated components onto the first and second spinous processes, respectively.

14. The system of claim 11, wherein the decompression knife comprises an elongated shaft having an elongated spade at a distal end and a handle at a proximal end and wherein the elongated spade comprises a concave inner surface, a convex outer surface, and a cutting edge terminating to a sharp point.

15. The system of claim 14, wherein the elongated spade comprises an electrically insulating material and the cutting edge comprises an electrically conducting material and wherein the cutting edge is connected to a power source and is used to cauterize tissue while cutting.

16. The system of claim 11, wherein the broach cutter comprises an elongated shaft having a cutting blade at a distal end and a handle at a proximal end and wherein the cutting blade comprises a hollow parallelepiped having a sharp cutting leading edge, a superior surface with a plurality of cutting edges, and an inferior surface with a plurality of cutting edges.

17. The system of claim 11, wherein the insertion tool comprises first and second elongated inserter components and wherein each elongated inserter component comprises an elongated outer tubular component and a stylet configured to slide within the outer tubular component and wherein the outer tubular component comprises a cutout at a distal end shaped and sized to laterally engage a cylindrical projection of the first or second elongated components.

18. The system of claim 17, wherein the stylet comprises a stylet elongated shaft and a spring surrounding the stylet elongated shaft and wherein a distal end of the stylet elongated shaft has a cross-sectional geometry matching the geometry of a top opening in a set screw of the interspinous spinal implant and wherein the stylet is configured to lock the first or second elongated components onto the distal end of the tubular component, by pressing down and rotating the stylet elongated shaft.

19. The system of claim 11, wherein the compressor tool comprises first and second components and a jaw component and wherein the first and second components are linked together via a multiaxially rotatable pivot link and wherein the distal end of the second component comprises a screw that attaches to the jaw component.

20. The system of claim 19, wherein the jaw component comprises a fixed jaw and a movable jaw and wherein the movable jaw is configured to slidably move within the fixed jaw via rotational motion of the second component and wherein the fixed jaw and the movable jaw are configured to engage and compress together the first and second elongated inserter components, respectively.

* * * * *